US008568730B2

(12) United States Patent
Wilkes

(10) Patent No.: US 8,568,730 B2
(45) Date of Patent: Oct. 29, 2013

(54) COMPOSITIONS FOR USE IN THE TREATMENT OF CHRONIC OBSTRUCTIVE PULMONARY DISEASES AND ASTHMA

(75) Inventor: David S. Wilkes, Indianapolis, IN (US)

(73) Assignee: Indiana University Research & Technology Corporation, Indianapolis, IN (US)

(*) Notice: Subject to any disclaimer, the term of this patent is extended or adjusted under 35 U.S.C. 154(b) by 0 days.

(21) Appl. No.: 13/265,847

(22) PCT Filed: Apr. 22, 2010

(86) PCT No.: PCT/US2010/032007
§ 371 (c)(1),
(2), (4) Date: Oct. 21, 2011

(87) PCT Pub. No.: WO2010/124058
PCT Pub. Date: Oct. 28, 2010

(65) Prior Publication Data
US 2012/0052081 A1    Mar. 1, 2012

Related U.S. Application Data

(60) Provisional application No. 61/266,048, filed on Dec. 2, 2009, provisional application No. 61/171,705, filed on Apr. 22, 2009.

(51) Int. Cl.
*A61K 39/00*   (2006.01)
(52) U.S. Cl.
USPC ...... 424/184.1; 514/12.2; 514/21.2; 514/17.2
(58) Field of Classification Search
None
See application file for complete search history.

(56) References Cited

U.S. PATENT DOCUMENTS

| 3,169,094 | A | 2/1965 | Wretlind |
| 4,237,224 | A | 12/1980 | Cohen et al. |
| 4,554,101 | A | 11/1985 | Hopp |
| 4,683,195 | A | 7/1987 | Mullis et al. |
| 4,683,202 | A | 7/1987 | Mullis |
| 4,751,180 | A | 6/1988 | Cousens et al. |
| 4,800,159 | A | 1/1989 | Mullis et al. |
| 4,883,750 | A | 11/1989 | Whiteley et al. |
| 4,935,233 | A | 6/1990 | Bell et al. |
| 5,633,234 | A | 5/1997 | August et al. |
| 5,837,458 | A | 11/1998 | Minshull et al. |
| 6,288,118 | B1 * | 9/2001 | Nieman et al. ........... 514/572 |
| 7,348,005 | B2 | 3/2008 | Wilkes |
| 7,759,075 | B2 * | 7/2010 | Wilkes et al. ........... 435/7.21 |
| 2012/0052081 | A1 | 3/2012 | Wilkes |

FOREIGN PATENT DOCUMENTS

| EP | 320308 | 6/1989 |
| EP | 329822 | 8/1989 |
| GB | 2202328 | 9/1988 |
| WO | WO 87/06270 | 10/1987 |
| WO | WO 88/10315 | 12/1988 |
| WO | WO 89/06700 | 7/1989 |
| WO | WO 89/09284 | 10/1989 |
| WO | WO 02/053092 | * 10/2002 |
| WO | WO 2007/120947 | 10/2007 |
| WO | WO/2007120947 | * 10/2007 |

OTHER PUBLICATIONS

Goodnow CC., Lancet. Jun. 30, 2001;357(9274):2115-21.*
Skyler, J.S., et al. Diabetes Care. 2005;28:1068-1076.*
Pozzilli, P., et al. Diabetol. 2000;43:1000-1004.*
Dong, V.M., et al. Ped. Transplant.. 1999;161:181-189.*
Bell, J.J. et al. J. Immunol. 2008;180:1508-1516.*
Kraus, T.A., and Mayer, L. Curr. Opin. Gastroenterol. 2005;21:692-696.*
Schroeder, R.A., et al. J. Surg. Sci. Res. 2003;111:109-119.*
Marketletter, Sep. 13, 1999, 2 pages.*
International Search Report and Written Opinion for International Application No. PCT/US2010/032007, mailed Oct. 13, 2010.
International Preliminary Report on Patentability for International Application No. PCT/US2010/032007, dated Oct. 25, 2011.
Alpan et al., "The Role of Dendritic Cells, B Cells, and M Cells in Gut-Oriented Immune Responses," *J. Immunol.* 166:4843-52, 2001.
Altschul et al., "Gapped BLAST and PSI-BLAST: a new generation of protein database search programs," *Nucleic Acids Research*, 25:3389-3402, 1997.
Altschul et al., "Basic Local Alignment Search Tool," *J. Mol. Biol.*, 215:403-410, 1990.
Bettelli et al., "Reciprocal developmental pathways for the generation of pathogenic effector $T_H17$ and regulatory T cells," *Nature*, 11:441(7090):235-8, 2006.
Bitter et al., "Expression and Secretion Vectors for Yeast," *Methods Enzymol.*, 153:516-544, 1987.
Broglie, R. et al., "Light-Regulated Expression of a Pea Ribulose-1,5-Bisphosphate Carboxylase Small Subunit Gene in Transformed Plant Cells," *Science*, 224:838-843, 1984.
Burlingham et al., "IL-17-dependent cellular immunity to collagen type V predisposes to obliterative bronchiolitis in human lung transplants," *J. Clin. Invest.* 117:3498-3506, 2007.
Chen et al., "Peripheral deletion of antigen-reactive T cells in oral tolerance," *Nature*, 376:177-180, 1995.
Chen et al., "Regulatory T-cell clones induced by oral tolerance: suppression of autoimmune encephalomyelitis," *Science*, 265:1237-1240 1994.
Chiang et al., "Type V(A-B) collagen induces platelet aggregation," *J. Lab. Clin. Med.*, 95:99-107, 1980.
Colbere-Garapin, F. et al, "A New Dominant Hybrid Selective Marker for Higher Eukaryotic Cells," *J. Mol. Biol.*, 150:1-14, 1981.
Coruzzi, G. et al., "Tissue specific and light-regulated expression of a pea nuclear gene encoding the small subunit of ribulose-1,5-bisphosphate carboxylase," *Embo J.* 3:1671-1680, 1984.
Cremer et al., "Type XI collagen-induced arthritis in the Lewis rat: characterization of cellular and humoral immune responses to native types XI, V, and II collagen and constituent α-chains," *J. Immunol.* 153:824-832, 1994.
Danzer et al., "Cytokine interactions in human mixed lymphocyte culture," *Transplantation*, 57(11):1638-1642, 1994.

(Continued)

Primary Examiner — Maher Haddad
(74) Attorney, Agent, or Firm — Cooley LLP

(57) ABSTRACT

The present invention provides compounds and methods for treating or preventing pulmonary diseases include COPD and asthma. In particular, the present invention provides for compounds comprising type V collagen, or tolerizing fragments thereof, for the treatment of COPD and asthma.

7 Claims, 6 Drawing Sheets

(56) References Cited

OTHER PUBLICATIONS

Dayhoff, M.O. (ed.) Atlas of Protein Sequence and Structure, National Biomedical Research Foundation, Washington DC, 5(3):345-358, 1978.
Deavin et al., "Statistical Comparison of Established T-Cell Epitope Predictors Against a Large Database of Human and Murine Antigens," *Mol. Immunol.* 33(2):145-155, 1996.
DeMeester et al., "The Bimodal Expression of Tumor Necrosis Factor-α in Association with Rat Lung Reimplantation and Allograft Rejection," *J. Immunol.*, 150(6):2494-2505, 1993.
Engelhard, E. K. et al, "The insect tracheal system: A conduit for the systemic spread of Autographa californica M nuclear polyhedrosis virus," *Proc. Natl. Acad. Sci.*, 91:3224-3227, 1994.
Faria et al., "Oral tolerance: mechanisms and therapeutic applications," *Adv. Immunol.*, 73:153-264, 1999.
Fedoseyeva et al., "De Novo Autoimmunity to Cardiac Myosin After Heart Transplantation and Its Contribution to the Rejection Process," *J Immunol*, 162:6836-42, 1999.
Fouser et al., "Th17 cytokines and their emerging roles in inflammation and autoimmunity," *Immunol Rev.*, 226:87-102, 2008.
Garrovillo et al., "Indirect allorecognition in acquired thymic tolerance: induction of donor-specific tolerance to rat cardiac allografts by allopeptide-pulsed host dendritic cells," *Transplantation*, 68:1827-1834, 1999.
Hancock et al., "Oral, but not intravenous, alloantigen prevents accelerated allograft rejection by selective intragraft Th2 cell activation," *Transplantation*, 55:1112-1118, 1993.
Hanson et al., "The human α 2(XI) collagen gene (COL11A2) maps to the centromeric of the major histocompatibility complex on chromosome 6," *Genomics*, 5:925-931, 1989.
Hartman, S. C. And Mulligan, R. C. "Two dominant-acting selectable markers for gene transfer studies in mammalian cells," *Proc. Natl. Acad. Sci.*, 85:8047-51, 1988.
Hein, J., "Unified Approach to Alignment and Phylogenes," *Methods in Enzymology*, 183:626-645, Academic Press, Inc., San Diego, CA, 1990.
Henikoff et al., "Amino Acid substitution matrices from protein blocks," *Proc. Natl. Acad. Sci.*,89:10915, 1992.
Higgins, D.G. And Sharp, P.M., "Fast and sensitive multiple sequence alignments on a microcomputer," *CABIOS*, 5:151-153, 1989.
Hirt et al., "Development of obliterative bronchiolitis after allogeneic rat lung transplantation: Implication of acute rejection and the time point of treatment," *J. Heart Lung Transplant.*, 18:542-548, 1999.
Hobbs, S. or Murry, L. E. in McGraw Hill Yearbook of Science and Technology, McGraw Hill, New York, N.Y.; pp. 191-196, 1992.
Horn, T. et al., "Synthesis of oligonucleotides on cellulose. Part II: design and synthetic strategy to the synthesis of 22 oligodeoxynucleotides coding for Gastric Inhibitory Polypeptide (GIP)," *Nucl. Acids Res. Symp. Ser.*, 7:225-232, 1980.
Huang et al.; "Stable mixed chimerism and tolerance using a nonmyeloablative preparative regimen in a large-animal model," *J. Clin. Invest.*, 105:173-181, 2000.
Ishido et al., "Induction of donor-specific hyporesponsiveness and prolongation of cardiac allograft survival by jejunal administration of donor splenocytes," *Transplantation*, 68:1377-1382, 1999.
Iyer et al., "Characterization and biologic significance of immunosuppressive peptide D2702.75-84(E α V) binding protein," *J. Bio. Chem.*, 273(5):2692-2697, 1998.
Jeffery, P. K., "Remodling in asthma and chronic obstructive lung disease," *American Journal of Respiratory and Critical Care Medicine*, 164(10-Pt.2):S28-S38, 2001.
Joo et al., "T-cell mediated responses in a murine model of orthotopic corneal transplantation," *Invest. Ophthalmol. Vis. Sci.*, 36:1530-1540, 1995.
Kang, et al., "Cutting Edge: Immunosuppressant as Adjuvant for Tolerogenic Immunization," *J. Immunol.*,180: 5172-5176, 2008.
Kapp J. A. and Bucy R. P., "CD8+ suppressor T cells resurrected," *Hum Immunol.*, 69(11):715-20, 2008.

Konomi et al., "Localization of Type V Collagen and Type IV Collagen in Human Cornea, Lung, and Skin," *Am. J. Pathol.*, 116:417-426, 1984.
Krensky et al., "HLA-derived peptides as novel immunosuppressives," *Nephroi. Dial. Transplant.*, 12:865-878, 1997.
Kroll, D. J. et al., "A Multifunctional Prokaryotic Protein Expression System: Overproduction, Affinity Purification, and Selective Detection," *DNA and Cell Biol.*, 12:441-453, 1993.
Logan, J. And Shenk, T., "Adenovirus tripartite leader sequence enhances of mRNAs late after infection," *Proc. Natl. Acad. Sci.*, 81:3655-3659, 1984.
Lowry et al., "Immune Mechanisms in Organ Allograft Rejection. VI. Delayed-Type Hypersensitivity and Lymphotoxin in Experimental Renal Allograft Rejection," *Transplantation*, 40:183-188, 1985.
Lowy, I., "Isolation of Transforming DNA: Cloning the Hamster aprt Gene," *Cell*, 22:817-23, 1980.
Maddox, D. E. et al., "Elevated Serum Levels in Human Pregnancy of a Molecule Immunochemically Similar to Eosinophil Granule Major Basic Protein," *J. Exp. Med.*, 158:1211-1216, 1983.
Madri et al., "Isolation and Tissue Localization of Type AB Collagen From Normal Lung Parenchyma Human Pathology," 11:353-366, 1980.
Madri et al., "Collagen Polymorphism in the Lung, An Immunochemical Study of Pulmonary Fibrosis," *Am. J. Pathol.*, 94:323-332, 1979.
Marck et al., "Lung Transplantation in the Rat. III. Functional Studies in Iso- and Allografts," *J. Surgical Res.*, 35:149-158, 1983.
Matsumura et al., "Assessment of Pathological Changes Associated with Chronic Allograft Rejection and Tolerance in Two Experimental Models of Rat Lung Transplantation," *Transplantation*, 59:1509-1517, 1995.
Merrifield, "Solid Phase Peptide Synthesis, I. The Synthesis of a Tetrapeptide," *J. Am. Chem. Soc.*, 85:2149-2154, 1963.
Mizobuchi et al., "Differential Expression of Smad7 Transcripts Identifies the CD4+CD45RC$^{high}$ Regulatory T Cells That Mediate Type V Collagen-Induced Tolerance to Lung Allografts," *J. Immunol.* 171:1140-1147, 2003.
Moore, "Update in Asthma 2007," *Am J Respir Crit Care Med.*, 177(10):1068-1073, 2008.
Morphy et a., "Matrix Metalloproteinase Inhibitors: Current Status," *Current Medicinal Chemistry*, 2:743-762, 1995.
Morris et al., "Type XI Collagen is a Heterotrimer with the Composition (1 α, 2 α, 3 α) Retaining Non-triple-helical Domains," *J. Biological Chem.*, 262:11345-11350, 1987.
Murphy et al., "Inhibition of allorecognition by a human class II MHC-derived peptide through the induction of apoptosis," *J. Clin. Invest.*, 103:859-867, 1999.
Murphy et al.; Genetic construction, expression, and melanoma-selective cytotoxicity of a diphtheria toxin-related a-melanocyte-stimulating hormone fusion protein, *Proc. Natl. Acad. Sci.*, 83:8258-8262, 1986.
Myers, E.W. And Muller W., "Optimal alignments in linear space," *CABIOS*, 4:(1):11-17, 1988.
Needleman et al., "A General Method Applicable to the Search for Similarities in the Amino Acid Sequence of Two Proteins," *J. Mol. Biol.*, 48:443-453, 1970.
Nößner et al., "HLA-derived Peptides which Inhibit T Cell Function Bind to Members of the Heat-Shock Protein 70 Family," *J. Exp. Med.*, 183:339-348, 1996.
Oluwole et al., "Induction of Transplantation Intolerance to Rat Cardiac Allografts by Intrathymic Inoculation of Allogeneic Soluble Peptides," *Transplantation*, 56(6):1523-1527, 1993.
Palmans, E. et al., "Repeated allergen exposure changes collagen composition in airways of sensitised Brown Norway rats," *The European Respiratory Journal*, 20(2):280-285, 2002.
Parker et al., "Scheme for Ranking Potential HLA-A2 Binding Peptides Based on Independent Binding of Individual Peptide Side-Chains," *J. Immunol.*, 152:163-175, 1994.
Pearson et al., "Improved tools for biological sequence comparison," *Proc. Natl. Acad. Sci.*, 85:2444-2448, 1988.
Porath, J. et al., "Immobilized Metal Ion Affinity Chromatography," *Prot. Exp. Purif.* 3:263-281, 1992.

(56) References Cited

OTHER PUBLICATIONS

Porter et al., "Recent developments in matrix metalloproteinase inhibitors," *Exp. Opin. Ther. Patents*, 5(12):1287-1296, 1995.
Prop et al., "Lung Allograft Rejection in the Rat. I. Accelerated Rejection Caused by Graft Lymphocytes," *Transplantation*, 40:25-30, 1985.
Prop et al., "Lung Allograft Rejection in the Rat. II. Specific immunological Properties of Lung Grafts," *Transplantation*, 40(2):126-131, 1985.
Rammensee et al., "MHC ligands and peptide motifs: first listing" *Immunogenetics*, 41:178-228, 1995.
Rhodes, C. A. et al., "Transformation of Maize by Electroporation of Embryos," *Methods Mol. Biol.* 55:121-131, 1995.
Roberge, J. Y. et al., "A Strategy for a Convergent Synthesis of N-Linked Glycopeptides on a Solid Support," *Science*,269:202-204, 1995.
Robinson, "Comparison of Labeled Trees with Valency Three," *J. Comb. Theory*, 11:105-119, 1971.
Rothbard et al., "A sequence pattern common to T cell epitopes," *The EMBO Journal*, 7:93-100, 1988.
Saitou, N. And Nei, M, "The Neighbor-joining Method: A New Method for Reconstructing Phylogenetic Trees," *Mol. Biol. Evol.*, 4:406-425, 1987.
Sayegh et al., "Mechanisms of T Cell Recognition of Alloantigen," *Transplantation*, 57:(9)1295-1302, 1994.
Sayegh et al., "Novel immunotherapeutic strategies using MHC derived peptides," *Kidney Int. Suppl.*, 53:S13-20, 1996.
Sayegh et al., "Induction of immunity and oral tolerance with polymorphic class II major histocompatibility complex allopeptides in the rat," *Proc. Natl. Acad. Sci.*, 89:7762-7766, 1992.
Sayegh et al., "Down-regulation of the immune response to histocompatibility antigens and prevention of sensitization by skin allografts by orally administered alloantigen," *Transplantation*, 53:163-166, 1992.
Scharf, D. et al., "Heat Stress Promoters and Transcription Factors," *Results Probl. Cell Differ.*, 20:125 162, 1994.
Sekine et al., "Role of Passenger Leukocytes in Allograft Rejection—Effect of Depletion Donor Alveolar Macrophages on the Local Production of TNF-alpha, T Helper 1/Thelper 2 Cytokines, IgG Subclasses, and Pathology in a Rat Model of Lung Transplantation," *J. Immuno*l, 159:4084-4093, 1997.
Seyer et al., "Covalent Structure of Collagen: Amino Acid Sequence of Three Cyanogen Bromide-Derived Peptides from Human Alpha 1(V) Collagen Chain," *Arch. Biochem. Biophys.*, 271(1):120-129, 1989.
Sivasai et al., "Indirect Recognition of donor HILA class I Peptides in Lung Transplant Recipients with Bronchiolitis Obliterans Syndrome," *Transplantation*, 67(8):1094-1098, 1999.
Smith, Jr. et al., "Interaction of proteoglycans with pericellular (1 alpha, 2 alpha, 3 alpha) collagens of cartilage," *J. Biol. Chem.*, 260:10761-10767, 1985.
Smith and Waterman, "Comparison of Biosequences Add," *APL. Math* 2:482-489, 1981.
Strober et al., "Tolerance and Immunity in the Mucosal Immune System," *Res. Immunol.*, 148:489-599, 1997.
Takamatsu, N., "Expression of bacterial chloramphenicol acetyltransferase gene in tobacco plans mediated by TMV-RNA," *EMBO J.*, 6:307-311, 1987.
Trulock, "Lung transplantation," *Am. J. Respir. Crit. Care Med.*, 155:789-818, 1997.
Vanbuskirk et al., "Patterns of allosensitization in allograft recipients: long-term allograft acceptance is associated with active alloantibody production in conjunction with active inhibition of alloreactive delayed-type hypersensitivity," *Transplantation*, 65:1115-1123, 1998.
Van Heeke, G. et al., "Expression of Human Asparagine in *Escherichia coli*," *J. Biol. Chem.*, 264:5503-5509, 1989.

Vignola et al., "Tissue Remodeling as a Feature of Persistent Asthma," *Journal of Allergy and Clinical Immunology*, 105(6):1041-1053, 2000.
Vogel et al., "Sensing extracellular matrix: An update on discoidin domain receptor function<" *Cellular Signalling*,18(8):1108-16, 2006.
Westra et al., "A Paradox in Heart and Lung Rejection," *Transplantation*, 49:826-828, 1990.
Weiner, "Oral tolerance: immune mechanisms and treatment of autoimmune diseases," *Imm. Today*, 7:335-44, 1997.
Whitacre et al., "Oral Tolerance in Experimental Autoimmune Encephalomyelitis. III. Evidence for Clonal Anergy," *J. Immunol.*, 147:2155-2163, 1991.
Wigler, M. et al., "Transformation of mammalian cells with an amplifable dominant-acting gene," *Proc. Natl. Acad. Sci.*, 77:3567-70, 1980.
Wigler, M. et al., "Transfer of Purified Herpes Virus Thymidine Kinase Gene to Cultured Mouse Cells," *Cell*, 11:223-32, 1977.
Wilbur et al., "Rapid similarity searches of nucleic acid and protein data banks," *Proc. Natl. Acad. Sci.*, 80:726-730, 1983.
Wilkes et al., "Allogeneic Bronchoalveolar Lavage Cells Induce the Histology and Immunology of Lung Allograft Rejection in Recipient Murine Lungs. Role of ICAM-1 on Donor cells," *Transplantation*, 67(6):890-896, 1999.
Wilkes et al., "Allogeneic Bronchoalveolar Lavage Cells Induce the Histology of Acute Lung Allograft Rejection, and Deposition of IGg2a in Recipient Murine Lungs," *J. Immunol.*, 155:2775-2783, 1995.
Wilkes et al., "Instillation of allogeneic lung macrophages and dendritic cells cause differential effects on local IfY-γ production, lymphocytic bronchitis, and vasculitis in recipient murine lungs," *J. Leukoc. Biol.*, 64:578-586, 1998.
Wilkes et al., "Cell-Mediated Immunity to Collagen V in Lung Transplant Recipients: Correlation with Collagen V Release into BAL fluid," *J. Heart Lung Transplant.*, 20:167, 2001.
Wilson et al., "Shared amino acid sequences between major histocompatibility complex class II glycoproteins, type XI collagen and Proteus mirabilis in rheumatoid arthritis," *Ann. Rheum. Dis.*, 54:216-220, 1995.
Winter, J. et al., "The Expression of Heat Shock Protein and Cognate Genes During Plant Development," *Results Probl. Cell Differ.*, 17:85-105, 1991.
Woessner, Jr., "The Determination of Hydroxyproline in Tissue and Protein Samples Containing Small Proportions of this Imino Acid," *Arch. Biochem. Biophys.*, 93:440-447, 1961.
Yagyu et al., "Comparison of mononuclear cell populations in brochoalveolar lavage fluid in acute rejection after lung transplantation and Mycoplasma infection in rats," *J. Heart Transplant.*, 9:516-525, 1990.
Yamagami et al., "Suppression of Allograft Rejection with anti-[alpha][beta] T Cell Receptor Antibody in Rat Corneal Transplantation," *Transplantation*, 67:600-604, 1999.
Yasufuku et al., "Prevention of Bronchiolitis Obliterans in Rat Lung allografts by Type V Collagen-Induced Oral Tolerance," *Transplantation*, 73:500-505, 2002.
Yasufuku et al., "Oral Tolerance Induction by Type V Collagen Downregulates Lung Allograft Rejection," *Am. J. Respir. Cell Mol. Biol.*, 25:26-34, 2001.
Yoshino et al., "Suppression of Antigen-Induced Arthritis in Lewis Rats by Oral Administration of Type II Collagen," *Arthritis Rheum.*, 38:1092-1096, 1995.
Yousem et al., "Revision of the 1990 working formulation for the classification of pulmonary allograft rejection: Lung rejection study group," *J. Heart Lung Transplant*, 15:1-15, 1996.
Zheng et al., "CTLA4 Signals Are Required to Optimally Induce Allograft Tolerance with Combined Donor-Specific Transfusion and Anti-CD154 Monoclonal Antibody Treatment," *J. Immunol.*, 162:4983-4990, 1999.

* cited by examiner

SEQUENCE LISTING

```
<160> NUMBER OF SEQ ID NOS: 6

<210> SEQ ID NO 1
<211> LENGTH: 8439
<212> TYPE: DNA
<213> ORGANISM: Homo sapiens

<400> SEQUENCE: 1
cgcactctcc gtccccgcgg ctggcgcagg acctcactcg agcggagcgc ccacggggag       60
cgggtcgcgg ggcggcggcg gcgaggagga ggcgagaagg agttggagga ggaggaggag      120
gaggcgaggg cgagctagcc cagcggggtc ccggccgccc cgcgggccaa agtcgagccc      180
tcccgcccgt gggcgagcgc gccagccgcc ccttccagaa cagccgccgc cacaaagaag      240 aacgggggt gccgaggtcc ccatgacctc ctaaagtggt gcggtccctg ctgagtgcgc       300
tgcccgggcc gtgacccgcg cccctgtgcg tccccgcgcg cctccgagcg ccccctgtgcg     360 ccccggcccg cgccccgccg gcatggacgt ccataccccgc tggaaagcgc gcagcgcgct    420
ccgcccgggc gcccccgctgc tgccccccgct gctgctgctg ctgctgtggg cgccgcctcc   480
gagccgcgca gctcagccag cagatctcct gaaggttcta gattttcaca acttgcctga    540
tggaataaca aagacaacag gcttttgcgc cacgcggcga tcttccaaag gcccggatgt    600
```

```
cgcttacaga gtcaccaaag acgcgcagct cagcgcaccc accaagcagc tgtaccctgc    660
gtctgcattt cccgaggact tctccatcct aacaactgtg aaagccaaga aaggcagcca    720
ggccttcctg gtctccatct acaacgagca gggtatccag cagattgggc tggagctggg    780
ccgctctccc gtcttcctct acgaggacca cacggggaag cctggcccgg aagactaccc    840
cctcttccgg ggcatcaacc tgtcagatgg caagtggcac agaattgctc tcagcgtcca    900
caagaaaaat gtcaccttga tcctcgactg taaaaagaag accaccaaat tcctcgaccg    960
cagcgaccac cccatgatcg acatcaatgg catcatcgtg tttggcaccc ggatcctgga   1020
tgaggaggtg tttgagggtg acatccagca gctgctcttt gtctcggacc accgggcagc   1080
ttatgattac tgtgagcact acagccctga ctgtgacacc gcagtacctg acaccccaca   1140
gtcgcaggac cccaatccag atgaatatta cacggaagga gacggcgagg gtgagaccta   1200
ttactacgaa taccccctact acgaagaccc cgaagaccta gggaaggagc caccccccag   1260
caagaagccc gtggaagctg ccaaagaaac cacagaggtc cccgaggagc tgaccccgac   1320
ccccacggaa gctgctccca tgcctgaaac cagtgaaggg gctgggaagg aagaggacgt   1380
cggcatcggg gactatgact acgtgcccag tgaggactac tacacgccct caccgtatga   1440
tgacctcacc tatggcgagg gggaggagaa ccccgaccag cccacagacc caggcgctgg   1500
ggccgaaatt cccaccagca ccgccgacac ctccaactcc tccaatccag ctccgcctcc   1560
aggggaaggt gcggatgact ggagggggga gttcactgag aaacgatcc ggaaccttga   1620 cgagaactac tacgacccct actacgaccc caccagctcc ccgtcggaga tcgggccggg   1680
aatgccggcg aaccaggata ccatctatga agggattgga ggacctcggg gcgagaaagg   1740
ccaaaaggga gaaccagcga ttatcgagcc gggcatgctc atcgagggcc cgcctggccc   1800
agaaggcccc gcgggtcttc ccggacctcc aggaaccatg gtcccactg gccaagtcgg   1860 ggaccctgga gaaaggggcc ccctggacg cccaggcctt cctggggccg atggcctgcc   1920
cggtcctcca ggaaccatgc tcatgctgcc cttccggttt ggaggtggcg gcgatgcggg   1980
ctccaaaggc cccatggtct cagcccagga gtcccaggcg caagccattc tccagcaggc   2040
caggttggca ctgagggac cagctggccc gatgggtctc acaggagac ctggccctgt   2100 gggtcccct gggagcggag gtttgaaggg cgagccggga gacgtgggc ctcagggtcc   2160 tcgaggtgtg caaggcccgc ctggtccggc cgggaagccc ggaagacggg gtcgggctgg   2220
gagtgatgga gccagaggaa tgcctggaca aactggcccc aagggtgacc ggggtttcga   2280
cggcctggct gggttgccag gcgagaaggg ccacagggt gaccctggtc cttccggcc   2340 accaggacct ccgggagacg atggagaaag gggtgacgac ggagaagttg gcccaggggg   2400
gctgcctggg gagcccggc cacgtggtct gcttgggccg aaggggcccc caggtcctcc   2460
cggacctccc ggtgtcacgg gtatggacgg ccagccgggg ccaaaaggaa atgtgggtcc   2520
ccagggagag cctggccccc caggacagca gggtaatcca ggcgcccagg tcttccagg   2580 cccccagggt gcaattggtc ctccaggaga aaagggtccc ttggggaaac aggccttcc   2640 aggaatgccc ggtgctgacg gacccccggg acacctggc aaagaaggcc ctccaggaga   2700
gaaaggaggt cagggtccac ctggccccca gggtccgatt ggctacccag gtcctcgagg   2760
agtcaagggg gccgatggca tccgtggtct gaagggcaca aagggcgaga agggtgaaga   2820 cggcttcct gggtttaaag agacatggg catcaagggt gatcgggggg agatcggccc   2880
acccggtccc aggggagaag atggccctga aggcccaaag gtcgcggag tcccaatgg   2940 tgaccccggt cctctgggac cccctgggga gaagggaaaa ctcggagtcc cagggttacc   3000
```

```
agggtatcca ggaagacaag gaccaaaggg ctctattgga ttccctggat ttcctggcgc      3060
caatggagag aagggcggca gggggacccc tggaaagcca ggaccgcggg ggcagcgagg      3120
cccaacgggt ccgaggggtg aaagaggccc ccggggcatc actgggaagc ctggccccaa      3180
gggcaactcc ggaggtgacg gcccagctgg ccctcctggt gaacgggggac ccaatggacc     3240 ccaaggaccc acaggatttc ctggaccaaa gggcccccct ggccctccag gcaaggatgg      3300
actcccagga caccctggac agagaggcga gactggtttc caaggcaaga ccggccctcc      3360 aggcccccc ggcgtggtcg gccctcaggg tcccacggga gaaacgggcc caatgggtga       3420
gcgtggccac cctgggcccc ctggaccccc cggtgaacag gggcttccgg gccttgctgg      3480
aaaagaaggg acgaagggtg acccaggccc tgcaggcctc cctgggaaag atggccctcc      3540
aggattacgt ggtttccctg ggaccgagg gcttcctggt ccagtgggag ctcttggact       3600
gaaaggcaat gaagggcccc ctggcccacc aggccctgcg ggatctccag gggagagagg      3660
tccagctgga gccgctgggc ccatcggaat tccaggggaga cctgggcccc agggaccccc     3720
agggccggca ggagagaaag gggctcctgg cgagaaaggc ccacaaggcc cagctggccg      3780
agacggtctc caggggcctg tggggctccc gggtccagct ggccctgtgg gtccccctgg     3840
agaagacgga gataagggag agatcgggga gccggggcag aaaggaagca aggggggacaa    3900 aggagaacag ggtcctcctg ggcctacagg tcctcaaggc cccatcggac agccaggccc     3960
ctctggagct gacggcgagc cggggcctcg gggccagcag ggccttttcg ggcagaaagg     4020
tgatgaaggt cccagaggct ttcctggacc ccctgggcca gtggggctgc agggtttgcc     4080
aggacctcca ggcgagaagg gtgagacagg agacgtgggc cagatgggcc ccccgggtcc     4140
ccctggcccc cgaggaccct ccggagctcc aggtgctgat ggcccacaag gtccccagg      4200 tggaatagga aaccctggtg cagtgggaga aagggcgag cctggcgaag caggtgagcc      4260
tggccttccg ggagaaggcg gccccccggg acccaaagga gaaaggggag agaagggcga     4320
gtcaggccct tcaggtgctg ccggaccccc tggacccaaa ggccctcccg gagatgatgg     4380
tcccaaaggc agccctggcc cagtgggttt cctggagat cctggccccc ccggagagcc      4440
tggccccgcg ggtcaagatg gtccccctgg tgacaaagga gatgatggtg aacccgggca     4500
gacgggatcc cccggcccta ctggtgaacc aggtccatcg gggcctccag gaaaaagggg     4560
tccccccagc cccgcaggcc ccgaaggcag acagggagag aaaggggcca agggagaagc     4620
cggcttggaa ggcccctcctg ggaagactgg ccccatcggc ccccagggggg ccctgggaa    4680 gcccggaccg gatggccttc gagggatccc tggccctgtg ggagaacaag gtctcccagg     4740
atccccaggc ccggacggtc ccccggccc catgggtccc ccaggacttc ccggcctcaa      4800
aggagattct ggtcccaaag gtgaaaaggg tcatccagge ctgatcgggc tcatcggtcc     4860
tccgggtgaa cagggtgaga agggcgaccg tggtctccct ggcccccagg ctcctccgg     4920 tcctaaggga gaacagggta tcactggtcc ttctggcccg attgggcctc ctgggccccc     4980
tggcctgccg ggtccgcctg gtccaaaagg tgctaagggc cctcgggtc caactggccc     5040 gaagggtgag gcaggccacc caggaccccc aggcccccg ggcccccgg gagaggtcat       5100 ccagccctg ccaatccagg catccaggac gcggcgaaac atcgacgcca ccagctgct       5160 ggacgacggg aatggcgaga actacgtgga ctacgcggac ggcatggaag agatcttcgg     5220
ctctctcaac tctctgaagc tggagattga gcagatgaaa cggcccctgg gcacgcagca     5280
gaaccccgcc cgcacctgca aggacctgca gctctgccac cccgacttcc agatggtga     5340 atactgggtc gatcctaacc aaggatgctc cagggattcc ttcaaggttt actgcaactt     5400
```

```
cacagccggg gggtcgacat gcgtcttccc tgacaagaag tccgaagggg ccagaatcac    5460
ttcttggccc aaagaaaacc cgggctcctg gttcagtgaa ttcaagcgtg ggaaactgct    5520
ctcctatgtg gacgccgagg gcaaccctgt gggtgtggta cagatgacct tcctgcggct    5580
gctgagcgcc tctgcccacc agaacgtcac ctaccactgc taccagtcag tggcctggca    5640
ggacgcagcc acgggcagct acgacaaggc cctccgcttc ctgggctcca acgacgagga    5700
gatgtcctat gacaacaacc cctacatccg cgccctggtg gacggctgtg ctaccaagaa    5760
aggctaccag aagacggttc tggagatcga cacccccaaa gtggagcagg tgcccatcgt    5820
ggacatcatg ttcaatgact tcggtgaagc gtcacagaaa tttggatttg aagtggggcc    5880
ggcttgcttc atgggctagg agccgccgag cccgggctcc cgagagcaac ctcgtgacct    5940
cagcatgcca ttcgttcgtg agtgtcccgt gcacgtcctg accctggaca gtgaaggctt    6000
ctccctcccc tcccacctga cttcatctac gcctcggcac cacggggtgt gggacccccag   6060
cccggagaga acagagggaa ggagccgcgc ccccacctgg agctgaatca catgacctag    6120
ctgcacccca gcgcctgggc cgccccacg ctctgtccac acccacgcgc cccgggagcg    6180
gggccatgcc tccagccccc cagctcgccc gacccatcct gttcgtgaat aggtctcagg    6240
ggttgggggga gggactgcca gatttggaca ctatattttt ttctaaattc aacttgaaga    6300
tgtgtatttc ccctgacctt caaaaaatgt tccaaggtaa gcctcgtaaa ggtcatccca    6360
ccatcaccaa agcctccgtt tttaacaacc tccaacacga tccatttaga ggccaaatgt    6420
cattctgcag gtgccttccc gatggattaa aggtgcttat gttttgtga gttttaagta     6480
aatatttgta ttgtattgtt ataaatgtta agtgtgcctg gctttcaatc atgcacggaa    6540
acccagtctc agtcccacgg acagaatggg cgaggcatgg attctgggtt gcagtaccgt    6600
tctgattaga aataggaagt ctccccaccc ccgccctggc caagaacgtg caataaattg    6660
gaagtttgcc ccggggcagc aagaatttat gctgccattg aaaagcaggt accagtgccc    6720
cttttcagac agttttttgat tcgctctaga cttttttttt ttttaatagg gaaaaaattt    6780
gataattttc ttttttctac atgcacttaa gactaaaaca caggtttgga ttaattttat    6840
ttgcttcctt tttccgcttt tcttcccgca gagcctgatg ggagaatgtc cagggcaggg    6900
aaaccacatt ttttgtaggt gataactcaa tgaaaattgg tgcttatttt ttacacttct    6960
ctcttgtggc tctcttgtgg tgctatctat ctgttttaag gtctccttga aggcgcactg    7020
gggaccctgg ccatgcctcg ttctccctgc tttctttatc ctgttattgc ctccacagtc    7080
tgttgccaag gactctaaga tcaatgcacg tcactttcct ttccactggg caggatagcc    7140
aagcacactc cctcctgcgc tctcccgccc cggtgcgtcc actcccgagg gctgttatga    7200
ggactgggtt gtgcctactt gatttgaaaa cacacacaag caataaaaag cctcttcctg    7260
cattgtctgt ggtgtgacca tagcagatta tatttggttc ctgaatgttt gtggtgctaa    7320
tttctgtgtt tgttccaagc cgttcagtca tgccatgcgc tgcctcggta gatggagtaa    7380
tgtacaatga actccatgag tctctccagg gctgcctgca gcacgtcttt tccaagtagc    7440
ctatttggat tccatctca aatgtcctgg atgcgagcgt cagcggctcc agagctcggg     7500
gcgggtgagg tcccctttgg ggaacccttt cctggccatc gaggtcgggg ggctgccgtc    7560
tgtgggcagg aggacccgag gggcagccag gaaaggcgat ctcttcactg tgaaaagttg    7620
cccgggtgca gcgcctttc cttctaccat gggaaatgca ggctgggccc ttggggtgag    7680
cctgcgggc tctggtgctg tccccgaccc ccaccaccac cagaatgcag ttccagctta    7740
ggaagccaca aacaagccac ccaggaggaa caaaacaccg ccagcgtgga ttttccaaat    7800
```

-continued

| | | |
|---|---|---|
| ttccctggaa agtaagtctc gctcttgcca aagaaaagtc tggcttggag agtctctgga | 7860 |
| gcccaggatg ccagcatgtg ccaatgactg tcaccttcat ctcttcaaaa gaaaagccat | 7920 |
| agccgaggac tgtcccgcga ccccgtgga ctgcgtctag gtcatgtgat tctgttttca | 7980 |
| tttctcatcc catccaattt gtcctttct cctgtcattt tcttcctctg tggtcccttc | 8040 |
| aaagttgtta taatttgtac tgaacttcaa aatgtgtccc gttctcccca gaccactcta | 8100 |
| gccacagtat attgcaataa aattacttct tatatttgca gaaattcttt tggtgtaatt | 8160 |
| ttatttttc ctctcaatat atataattgg acaaacgctg gcaaaagaa aaaatggta | 8220 |
| agcaaaaaac ccaagataaa gtttcgagga catcaggcct tttgaaatac aatgtcaaat | 8280 |
| gacacattgt acggtttcaa aaaatccgct agacatgtca taagttttaa ctgtaatgcc | 8340 |
| caggaaagga tatcttaaaa tattctaaac ttgtgtaaca aaggaataat taactgtaat | 8400 |
| agttttcaa taaatcgagt tgggtgtttc caccgtaaa | 8439 |

<210> SEQ ID NO 2
<211> LENGTH: 1838
<212> TYPE: PRT
<213> ORGANISM: Homo sapiens

<400> SEQUENCE: 2

Met Asp Val His Thr Arg Trp Lys Ala Arg Ser Ala Leu Arg Pro Gly
 1               5                   10                  15

Ala Pro Leu Leu Pro Pro Leu Leu Leu Leu Leu Trp Ala Pro Pro
                 20                  25                  30

Pro Ser Arg Ala Ala Gln Pro Ala Asp Leu Leu Lys Val Leu Asp Phe
             35                  40                  45

His Asn Leu Pro Asp Gly Ile Thr Lys Thr Thr Gly Phe Cys Ala Thr
         50                  55                  60

Arg Arg Ser Ser Lys Gly Pro Asp Val Ala Tyr Arg Val Thr Lys Asp
 65                  70                  75                  80

Ala Gln Leu Ser Ala Pro Thr Lys Gln Leu Tyr Pro Ala Ser Ala Phe
                 85                  90                  95

Pro Glu Asp Phe Ser Ile Leu Thr Thr Val Lys Ala Lys Lys Gly Ser
             100                 105                 110

Gln Ala Phe Leu Val Ser Ile Tyr Asn Glu Gln Gly Ile Gln Gln Ile
         115                 120                 125

Gly Leu Glu Leu Gly Arg Ser Pro Val Phe Leu Tyr Glu Asp His Thr
130                 135                 140

Gly Lys Pro Gly Pro Glu Asp Tyr Pro Leu Phe Arg Gly Ile Asn Leu
145                 150                 155                 160

Ser Asp Gly Lys Trp His Arg Ile Ala Leu Ser Val His Lys Lys Asn
                 165                 170                 175

Val Thr Leu Ile Leu Asp Cys Lys Lys Lys Thr Thr Lys Phe Leu Asp
             180                 185                 190

Arg Ser Asp His Pro Met Ile Asp Ile Asn Gly Ile Ile Val Phe Gly
         195                 200                 205

Thr Arg Ile Leu Asp Glu Glu Val Phe Glu Gly Asp Ile Gln Gln Leu
     210                 215                 220

Leu Phe Val Ser Asp His Arg Ala Ala Tyr Asp Tyr Cys Glu His Tyr
225                 230                 235                 240

Ser Pro Asp Cys Asp Thr Ala Val Pro Asp Thr Pro Gln Ser Gln Asp
                 245                 250                 255

Pro Asn Pro Asp Glu Tyr Tyr Thr Glu Gly Asp Gly Glu Gly Glu Thr
             260                 265                 270

Tyr Tyr Tyr Glu Tyr Pro Tyr Tyr Glu Asp Pro Glu Asp Leu Gly Lys
            275                 280                 285
Glu Pro Thr Pro Ser Lys Lys Pro Val Glu Ala Ala Lys Glu Thr Thr
290                 295                 300
Glu Val Pro Glu Glu Leu Thr Pro Thr Pro Thr Glu Ala Ala Pro Met
305                 310                 315                 320
Pro Glu Thr Ser Glu Gly Ala Gly Lys Glu Glu Asp Val Gly Ile Gly
                325                 330                 335
Asp Tyr Asp Tyr Val Pro Ser Glu Asp Tyr Tyr Thr Pro Ser Pro Tyr
            340                 345                 350
Asp Asp Leu Thr Tyr Gly Gly Glu Glu Asn Pro Asp Gln Pro Thr
            355                 360                 365
Asp Pro Gly Ala Gly Ala Glu Ile Pro Thr Ser Thr Ala Asp Thr Ser
370                 375                 380
Asn Ser Ser Asn Pro Ala Pro Pro Gly Glu Gly Ala Asp Asp Leu
385                 390                 395                 400
Glu Gly Glu Phe Thr Glu Glu Thr Ile Arg Asn Leu Asp Glu Asn Tyr
                405                 410                 415
Tyr Asp Pro Tyr Tyr Asp Pro Thr Ser Ser Pro Ser Glu Ile Gly Pro
            420                 425                 430
Gly Met Pro Ala Asn Gln Asp Thr Ile Tyr Glu Gly Ile Gly Gly Pro
            435                 440                 445
Arg Gly Glu Lys Gly Gln Lys Gly Glu Pro Ala Ile Ile Glu Pro Gly
        450                 455                 460
Met Leu Ile Glu Gly Pro Pro Gly Pro Glu Gly Pro Ala Gly Leu Pro
465                 470                 475                 480
Gly Pro Pro Gly Thr Met Gly Pro Thr Gly Gln Val Gly Asp Pro Gly
                485                 490                 495
Glu Arg Gly Pro Pro Gly Arg Pro Gly Leu Pro Gly Ala Asp Gly Leu
            500                 505                 510
Pro Gly Pro Pro Gly Thr Met Leu Met Leu Pro Phe Arg Phe Gly Gly
            515                 520                 525
Gly Gly Asp Ala Gly Ser Lys Gly Pro Met Val Ser Ala Gln Glu Ser
        530                 535                 540
Gln Ala Gln Ala Ile Leu Gln Gln Ala Arg Leu Ala Leu Arg Gly Pro
545                 550                 555                 560
Ala Gly Pro Met Gly Leu Thr Gly Arg Pro Gly Pro Val Gly Pro Pro
                565                 570                 575
Gly Ser Gly Gly Leu Lys Gly Glu Pro Gly Asp Val Gly Pro Gln Gly
            580                 585                 590
Pro Arg Gly Val Gln Gly Pro Pro Gly Pro Ala Gly Lys Pro Gly Arg
            595                 600                 605
Arg Gly Arg Ala Gly Ser Asp Gly Ala Arg Gly Met Pro Gly Gln Thr
        610                 615                 620
Gly Pro Lys Gly Asp Arg Gly Phe Asp Gly Leu Ala Gly Leu Pro Gly
625                 630                 635                 640
Glu Lys Gly His Arg Gly Asp Pro Gly Pro Ser Gly Pro Pro Gly Pro
                645                 650                 655
Pro Gly Asp Asp Gly Glu Arg Gly Asp Asp Gly Glu Val Gly Pro Arg
            660                 665                 670
Gly Leu Pro Gly Glu Pro Gly Pro Arg Gly Leu Leu Gly Pro Lys Gly
            675                 680                 685
Pro Pro Gly Pro Pro Gly Pro Pro Gly Val Thr Gly Met Asp Gly Gln

```
                690            695            700
Pro Gly Pro Lys Gly Asn Val Gly Pro Gln Gly Glu Pro Gly Pro Pro
705                 710                 715                 720

Gly Gln Gln Gly Asn Pro Gly Ala Gln Gly Leu Pro Gly Pro Gln Gly
            725                 730                 735

Ala Ile Gly Pro Pro Gly Glu Lys Gly Pro Leu Gly Lys Pro Gly Leu
            740                 745                 750

Pro Gly Met Pro Gly Ala Asp Gly Pro Gly His Pro Gly Lys Glu
            755                 760                 765

Gly Pro Pro Gly Glu Lys Gly Gly Gln Gly Pro Pro Gly Pro Gln Gly
770                 775                 780

Pro Ile Gly Tyr Pro Gly Pro Arg Gly Val Lys Gly Ala Asp Gly Ile
785                 790                 795                 800

Arg Gly Leu Lys Gly Thr Lys Gly Glu Lys Gly Glu Asp Gly Phe Pro
                805                 810                 815

Gly Phe Lys Gly Asp Met Gly Ile Lys Gly Asp Arg Gly Glu Ile Gly
            820                 825                 830

Pro Pro Gly Pro Arg Gly Glu Asp Gly Pro Glu Gly Pro Lys Gly Arg
            835                 840                 845

Gly Gly Pro Asn Gly Asp Pro Gly Pro Leu Gly Pro Pro Gly Glu Lys
850                 855                 860

Gly Lys Leu Gly Val Pro Gly Leu Pro Gly Tyr Pro Gly Arg Gln Gly
865                 870                 875                 880

Pro Lys Gly Ser Ile Gly Phe Pro Gly Phe Pro Gly Ala Asn Gly Glu
                885                 890                 895

Lys Gly Gly Arg Gly Thr Pro Gly Lys Pro Gly Pro Arg Gly Gln Arg
            900                 905                 910

Gly Pro Thr Gly Pro Arg Gly Glu Arg Gly Pro Arg Gly Ile Thr Gly
            915                 920                 925

Lys Pro Gly Pro Lys Gly Asn Ser Gly Gly Asp Gly Pro Ala Gly Pro
930                 935                 940

Pro Gly Glu Arg Gly Pro Asn Gly Pro Gln Gly Pro Thr Gly Phe Pro
945                 950                 955                 960

Gly Pro Lys Gly Pro Pro Gly Pro Gly Lys Asp Gly Leu Pro Gly
            965                 970                 975

His Pro Gly Gln Arg Gly Glu Thr Gly Phe Gln Gly Lys Thr Gly Pro
            980                 985                 990

Pro Gly Pro Pro Gly Val Val Gly Pro Gln Gly Pro Thr Gly Glu Thr
            995                 1000                1005

Gly Pro Met Gly Glu Arg Gly His Pro Gly Pro Pro Gly Pro Pro Gly
    1010                1015                1020

Glu Gln Gly Leu Pro Gly Leu Ala Gly Lys Glu Gly Thr Lys Gly Asp
1025                1030                1035                1040

Pro Gly Pro Ala Gly Leu Pro Gly Lys Asp Gly Pro Pro Gly Leu Arg
                1045                1050                1055

Gly Phe Pro Gly Asp Arg Gly Leu Pro Gly Pro Val Gly Ala Leu Gly
            1060                1065                1070

Leu Lys Gly Asn Glu Gly Pro Pro Gly Pro Pro Gly Pro Ala Gly Ser
            1075                1080                1085

Pro Gly Glu Arg Gly Pro Ala Gly Ala Ala Gly Pro Ile Gly Ile Pro
            1090                1095                1100

Gly Arg Pro Gly Pro Gln Gly Pro Pro Gly Pro Ala Gly Glu Lys Gly
1105                1110                1115                1120
```

-continued

```
Ala Pro Gly Glu Lys Gly Pro Gln Gly Pro Ala Gly Arg Asp Gly Leu
            1125                1130                1135

Gln Gly Pro Val Gly Leu Pro Gly Pro Ala Gly Pro Val Gly Pro Pro
            1140                1145                1150

Gly Glu Asp Gly Asp Lys Gly Glu Ile Gly Glu Pro Gly Gln Lys Gly
            1155                1160                1165

Ser Lys Gly Asp Lys Gly Glu Gln Gly Pro Pro Gly Pro Thr Gly Pro
            1170                1175                1180

Gln Gly Pro Ile Gly Gln Pro Gly Pro Ser Gly Ala Asp Gly Glu Pro
1185                1190                1195                1200

Gly Pro Arg Gly Gln Gln Gly Leu Phe Gly Gln Lys Gly Asp Glu Gly
            1205                1210                1215

Pro Arg Gly Phe Pro Gly Pro Pro Gly Pro Val Gly Leu Gln Gly Leu
            1220                1225                1230

Pro Gly Pro Pro Gly Glu Lys Gly Glu Thr Gly Asp Val Gly Gln Met
            1235                1240                1245

Gly Pro Pro Gly Pro Pro Gly Pro Arg Gly Pro Ser Gly Ala Pro Gly
            1250                1255                1260

Ala Asp Gly Pro Gln Gly Pro Pro Gly Ile Gly Asn Pro Gly Ala
1265                1270                1275                1280

Val Gly Glu Lys Gly Glu Pro Gly Glu Ala Gly Glu Pro Gly Leu Pro
            1285                1290                1295

Gly Glu Gly Gly Pro Pro Gly Pro Lys Gly Glu Arg Gly Glu Lys Gly
            1300                1305                1310

Glu Ser Gly Pro Ser Gly Ala Ala Gly Pro Pro Gly Pro Lys Gly Pro
            1315                1320                1325

Pro Gly Asp Asp Gly Pro Lys Gly Ser Pro Gly Pro Val Gly Phe Pro
            1330                1335                1340

Gly Asp Pro Gly Pro Pro Gly Glu Pro Gly Pro Ala Gly Gln Asp Gly
1345                1350                1355                1360

Pro Pro Gly Asp Lys Gly Asp Asp Gly Glu Pro Gly Gln Thr Gly Ser
            1365                1370                1375

Pro Gly Pro Thr Gly Glu Pro Gly Pro Ser Gly Pro Pro Gly Lys Arg
            1380                1385                1390

Gly Pro Pro Gly Pro Ala Gly Pro Glu Gly Arg Gln Gly Glu Lys Gly
            1395                1400                1405

Ala Lys Gly Glu Ala Gly Leu Glu Gly Pro Pro Gly Lys Thr Gly Pro
            1410                1415                1420

Ile Gly Pro Gln Gly Ala Pro Gly Lys Pro Gly Pro Asp Gly Leu Arg
1425                1430                1435                1440

Gly Ile Pro Gly Pro Val Gly Glu Gln Gly Leu Pro Gly Ser Pro Gly
            1445                1450                1455

Pro Asp Gly Pro Pro Gly Pro Met Gly Pro Pro Gly Leu Pro Gly Leu
            1460                1465                1470

Lys Gly Asp Ser Gly Pro Lys Gly Glu Lys Gly His Pro Gly Leu Ile
            1475                1480                1485

Gly Leu Ile Gly Pro Pro Gly Glu Gln Gly Glu Lys Gly Asp Arg Gly
            1490                1495                1500

Leu Pro Gly Pro Gln Gly Ser Ser Gly Pro Lys Gly Glu Gln Gly Ile
1505                1510                1515                1520

Thr Gly Pro Ser Gly Pro Ile Gly Pro Pro Gly Pro Pro Gly Leu Pro
            1525                1530                1535

Gly Pro Pro Gly Pro Lys Gly Ala Lys Gly Ser Ser Gly Pro Thr Gly
            1540                1545                1550
```

Pro Lys Gly Glu Ala Gly His Pro Gly Pro Pro Gly Pro
    1555                1560                1565

Pro Gly Glu Val Ile Gln Pro Leu Pro Ile Gln Ala Ser Arg Thr Arg
    1570                1575                1580

Arg Asn Ile Asp Ala Ser Gln Leu Leu Asp Asp Gly Asn Gly Glu Asn
1585                1590                1595                1600

Tyr Val Asp Tyr Ala Asp Gly Met Glu Glu Ile Phe Gly Ser Leu Asn
            1605                1610                1615

Ser Leu Lys Leu Glu Ile Glu Gln Met Lys Arg Pro Leu Gly Thr Gln
        1620                1625                1630

Gln Asn Pro Ala Arg Thr Cys Lys Asp Leu Gln Leu Cys His Pro Asp
    1635                1640                1645

Phe Pro Asp Gly Glu Tyr Trp Val Asp Pro Asn Gln Gly Cys Ser Arg
    1650                1655                1660

Asp Ser Phe Lys Val Tyr Cys Asn Phe Thr Ala Gly Gly Ser Thr Cys
1665                1670                1675                1680

Val Phe Pro Asp Lys Lys Ser Glu Gly Ala Arg Ile Thr Ser Trp Pro
            1685                1690                1695

Lys Glu Asn Pro Gly Ser Trp Phe Ser Glu Phe Lys Arg Gly Lys Leu
        1700                1705                1710

Leu Ser Tyr Val Asp Ala Glu Gly Asn Pro Val Gly Val Val Gln Met
    1715                1720                1725

Thr Phe Leu Arg Leu Leu Ser Ala Ser Ala His Gln Asn Val Thr Tyr
    1730                1735                1740

His Cys Tyr Gln Ser Val Ala Trp Gln Asp Ala Ala Thr Gly Ser Tyr
1745                1750                1755                1760

Asp Lys Ala Leu Arg Phe Leu Gly Ser Asn Asp Glu Glu Met Ser Tyr
            1765                1770                1775

Asp Asn Asn Pro Tyr Ile Arg Ala Leu Val Asp Gly Cys Ala Thr Lys
        1780                1785                1790

Lys Gly Tyr Gln Lys Thr Val Leu Glu Ile Asp Thr Pro Lys Val Glu
    1795                1800                1805

Gln Val Pro Ile Val Asp Ile Met Phe Asn Asp Phe Gly Glu Ala Ser
    1810                1815                1820

Gln Lys Phe Gly Phe Glu Val Gly Pro Ala Cys Phe Met Gly
1825                1830                1835

<210> SEQ ID NO 3
<211> LENGTH: 6930
<212> TYPE: DNA
<213> ORGANISM: Homo sapiens

<400> SEQUENCE: 3
gaccgttgct tggcagacac tggatggtta tgagcctgaa caagctgaaa aggggcagga      60
aaagaagtgg aggcagcatt cttcctattt aaagctgcat cgcttgaaaa aagttttcgc     120
agactgtgct ggagctggtg ctgaaaaagg gggtttgcag aggctgccct ggggctggtg     180
ctgaaagaag agcccacagc tgacttcatg gtgctacaat aacctcagaa tctacttttc     240
actctcagga gaaccacat gtctaatatt tagacatgat ggcaaactgg gcggaagcaa      300
gacctctcct cattcttatt gttttattag ggcaatttgt ctcaataaaa gcccaggaag     360
aagacgagga tgaaggatat ggtgaagaaa tagcctgcac tcagaatggc cagatgtact     420
taaacaggga catttggaaa cctgccccct gtcagatctg tgtctgtgac aatggagcca     480
ttctctgtga caagatagaa tgccaggatg tgctggactg tgccgaccct gtaacgcccc     540

```
ctggggaatg ctgtcctgtc tgttcacaaa cacctggagg tggcaataca aattttggta      600
gaggaagaaa gggacaaaag ggagaaccag gattagtgcc tgttgtaaca ggcatacgtg      660
gtcgtccagg accggcagga cctccaggat cacaggggacc aagaggagag cgagggccaa     720
aaggaagacc tggccctcgt ggacctcagg gaattgatgg agaaccaggt gttcctggtc      780
aacctggtgc tccaggacct cctggacatc cgtcccaccc aggacccgat ggcttgagca      840
ggccgttttc agctcaaatg ctgggttgg atgaaaaatc tggacttggg agtcaagtag       900
gactaatgcc tggctctgtg gtcctgttg cccaagggg accacagggt ttacaaggac        960
agcaaggtgg tgcaggacct acaggacctc ctggtgaacc tggtgatcct ggaccaatgg     1020
gtccgattgg ttcacgtgga ccagagggcc ctcctggtaa acctggggaa gatggtgaac     1080
ctggcagaaa tggaaatcct ggtgaagtgg gatttgcagg atctccggga gctcgtggat    1140
ttcctggggc tcctggtctt ccaggtctga gggtcaccg aggacacaaa ggtcttgaag     1200
gccctaaagg tgaagttgga gcacctggtt ccaagggtga agctggcccc actggtccaa    1260
tgggtgccat gggtcctctg gtccgaggg gaatgccagg agagagggg agacttgggc       1320 cacagggtgc tcctggacaa cgaggtgcac atggtatgcc tggaaaacct ggaccaatgg    1380
gtcctcttgg gataccaggc tcttctggtt ttccaggaaa tcctggaatg aagggagaag    1440
caggtcctac aggggcgcga ggccctgaag gtcctcaggg gcagagaggt gaaactgggc    1500
ccccaggtcc agttggctct ccaggtcttc ctggtgcaat aggaactgat ggtactcctg    1560
gtgccaaagg cccaacgggc tctccgggta cctctggtcc tcctggctca gcagggcctc    1620
ctggatctcc aggacctcag ggtagcactg gtcctcaggg aattcgaggc caaccgggtg    1680
atccaggagt tccaggtttc aaaggagaag ctggcccaaa aggggaacca gggccacatg    1740
gtattcaggg tccgataggc ccacccggtg aagaaggcaa aagaggtccc agaggtgacc    1800
caggaacagt tggtcctcca gggccagtgg gagaaagggg tgctcctggc aatcgtggtt    1860
ttccaggctc tgatggttta cctgggccaa agggtgctca aggagaacgg ggtcctgtag    1920
gttcttcagg acccaaagga gccagggggg atccaggacg tccagggaa cctgggcttc     1980 caggtgctcg gggtttgaca ggaaatcctg gtgttcaagg tcctgaagga aaacttggac    2040
ctttgggtgc gccaggggaa gatggccgtc caggtcctcc aggctccata ggaatcagag    2100
ggcagcccgg gagcatgggc cttccaggcc ccaaaggtag cagtggtgac cctgggaaac    2160
ctggagaagc aggaaatgct ggagttcctg ggcagagggg agctcctgga aaagatggtg    2220
aagttggtcc ttctggtcct gtgggcccgc cgggtctagc tggtgaaaga ggagaacaag    2280
gacctccagg ccccacaggt tttcaggggc ttcctggtcc tccagggcct cctggagaag    2340
gtggaaaacc aggtgatcaa ggtgttcctg gagatcccgg agcagttggc ccgttaggac    2400
ctagaggaga acgaggaaat cctgggggaaa gaggagaacc tgggataact ggactccctg    2460
gtgagaaggg aatggctgga ggacatggtc ctgatggccc aaaaggcagt ccaggtccat    2520
ctgggacccc tggagataca ggcccaccag gtcttcaagg tatgccggga gaaagaggaa    2580
ttgcaggaac tcctggcccc aagggtgaca gaggtggcat aggagaaaaa ggtgctgaag    2640
gcacagctgg aaatgatggt gcaagaggtc ttccaggtcc tttgggccct ccaggtccgg    2700
caggtcctac tggagaaaag ggtgaacctg gtcctcgagt tttagttggc cctcctggct    2760
cccggggcaa tcctggttct cgaggtgaaa atgggccaac tggagctgtt ggttttgccg    2820 gacccccaggg tcctgacgga cagcctggag taaaaggtga acctggagag ccaggacaga    2880
agggagatgc tggttctcct ggaccacaag gtttagcagg atccccctggc cctcatggtc    2940
```

```
ctaatggtgt tcctggacta aaaggtggtc gaggaaccca aggtccgcct ggtgctacag     3000
gatttcctgg ttctgcgggc agagttggac ctccaggccc tgctggagct ccaggacctg     3060
cgggacccct aggggaaccc gggaaggagg acctccagg tcttcgtggg gaccctggct      3120
ctcatgggcg tgtgggagat cgaggaccag ctggccccc tggtggccca ggagacaaag      3180
gggacccagg agaagatggg caacctggtc cagatggccc ccctggtcca gctggaacga     3240
ccgggcagag aggaattgtt ggcatgcctg ggcaacgtgg agagagaggc atgcccggcc     3300
taccaggccc agcgggaaca ccaggaaaag taggaccaac tggtgcaaca ggagataaag     3360
gtccacctgg acctgtgggg cccccaggct ccaatggtcc tgtagggaa cctggaccag      3420 aaggtccagc tggcaatgat ggtaccccag gacgggatgg tgctgttgga aacgtggtg      3480 atcgtggaga ccctgggcct gcaggtctgc caggctctca gggtgcccct ggaactcctg     3540
gccctgtggg tgctccagga gatgcaggac aaagaggaga tccgggttct cggggtccta    3600
taggaccacc tggtcgagct gggaaacgtg gattacctgg accccaagga cctcgtggtg    3660
acaaaggtga tcatggagac cgaggcgaca gaggtcagaa gggccacaga ggctttactg    3720
gtcttcaggg tcttcctggc cctcctggtc caatggtga caaggaagt gctggaatcc      3780 ctggaccatt tggcccaaga ggtcctccag gcccagttgg tccttcaggt aaagaaggaa     3840
accctgggcc acttgggcca attggacctc caggtgtacg aggcagtgta ggagaagcag    3900
gacctgaggg ccctcctggt gagcctggcc cacctggccc tccgggtccc cctggccacc    3960
ttacagctgc tcttggggat catgggggc actatgatga agcatgcca gatccacttc      4020 ctgagtttac tgaagatcag gcggctcctg atgacaaaaa caaacggac ccaggggttc     4080 atgctaccct gaagtcactc agtagtcaga ttgaaaccat gcgcagcccc gatggctcga    4140
aaaagcaccc agcccgcacg tgtgatgacc taaagctttg ccattccgca aagcagagtg    4200
gtgaatactg gattgatcct aaccaaggat ctgttgaaga tgcaatcaaa gtttactgca    4260
acatggaaac aggagaaaca tgtatttcag caaacccatc cagtgtacca cgtaaaacct    4320
ggtgggccag taaatctcct gacaataaac ctgtttggta tggtcttgat atgaacagag    4380
ggtctcagtt cgcttatgga gaccaccaat cacctaatac agccattact cagatgactt    4440
ttttgcgcct tttatcaaaa gaagcctccc agaacatcac ttacatctgt aaaaacagtg    4500
taggatacat ggacgatcaa gctaagaacc tcaaaaaagc tgtggttctc aaaggggcaa    4560
atgacttaga tatcaaagca gagggaaata ttagattccg gtatatcgtt cttcaagaca    4620
cttgctctaa gcggaatgga aatgtgggca agactgtctt tgaatataga acacagaatg    4680
tggcacgctt gccccatcata gatcttgctc ctgtggatgt tggcggcaca gaccaggaat    4740
tcggcgttga aattgggcca gtttgttttg tgtaaagtaa gccaagacac atcgacaatg    4800
agcaccacca tcaatgacca ccgccattca caagaacttt gactgtttga agttgatcct    4860
gagactcttg aagtaatggc tgatcctgca tcagcattgt atatatggtc ttaagtgcct    4920
ggcctcctta tccttcagaa tatttatttt acttacaatc ctcaagtttt aattgatttt    4980
aaatattttt caatacaaca gtttaggttt aagatgacca atgacaatga ccacctttgc    5040
agaaagtaaa ctgattgaat aaataaatct ccgttttctt caatttattt cagtgtaatg    5100
aaaaagttgc ttagtattta tgaggaaatt cttcttcctg gcaggtagct taagagtgg     5160 ggtatataga gccacaacac atgtttattt tgcttggctg cagttgaaaa atagaaatta    5220 gtgcccttt tgtgacctctc attccaagat tgtcaattaa aaatgagttt aaaatgttta    5280
acttgtgatc gagacctaca tgcatgtctt gatattgtgt aactataata gagactcttt    5340
```

-continued

```
aaggagaatc ttaaaaaaaa aaaaacgttt ctcactgtct taaatagaat ttttaaatag    5400
tatatattca gtggcatttt ggagaacaaa gtgaatttac ttcgacttct taaattttg     5460 taaaagacta aagtttaga catctttctc attcaaattt aaagatatct ttctcctctt     5520
gatcaatcta tcaatattga tagaagtcac actagtatat accatttaat acatttacac   5580
tttcttattt aagaagatat tgaatgcaaa ataattgaca tatagaactt tacaaacata   5640
tgtccaagga ctctaaattg agactcttcc acatgtacaa tctcatcatc ctgaagccta   5700
taatgaagaa aaagatctag aaactgagtt gtggagctga ctctaatcaa atgtgatgat   5760
tggaattaga ccatttggcc tttgaacttt cataggaaaa atgacccaac atttcttagc   5820
atgagctacc tcatctctag aagctgggat ggacttacta ttcttgttta tattttagat   5880
actgaaaggt gctatgcttc tgttattatt ccaagactgg agataggcag ggctaaaaag   5940
gtattattat ttttccttta atgatggtgc taaaattctt cctataaaat tccttaaaaa    6000
taaagatggt ttaatcacta ccattgtgaa aacataactg ttagacttcc cgtttctgaa    6060
agaaagagca tcgttccaat gcttgttcac tgttcctctg tcatactgta tctggaatgc   6120
tttgtaatac ttgcatgctt cttagaccag aacatgtagg tccccttgtg tctcaatact   6180
ttttttttct taattgcatt tgttggctct attttaattt ttttcttta aaataaacag     6240 ctgggaccat cccaaaagac aagccatgca tacaactttg gtcatgtatc tctgcaaagc   6300
atcaaattaa atgcacgctt ttgtcatgtc agtggttttt gttttgtgaa attcctttga   6360
ccatattaga tctatttcat ttccaatagt gaaaaggaga tgtggtggta tactttgttt   6420
gccatttgtt taaaagatac aacggatacc ttctatcatg tatgtactgg cttataaatg   6480
aaaatctatc tacaacatta cccacaaagg caacatgaca ccaattatca ctgcctctgc   6540
ccttaaaaat gtcagagtag tattattgat aaaaagggca agcaatagat ttttcatgac   6600
tgaataaact gtaataataa aacatatgtc tcaaagtgta tcacatatga atttagccta   6660
attgttttca gtttcattct caatatttag tttacaacat catttttcccc taaactggtt   6720 atatttgac ctgtatatct taaatttgag tattttatg cctaaataca tgtgtgagtt      6780
ttgtttgact tccaagtcca aactataaga ttatataagt tcatatagat gaatcagaaa   6840
tatgtggtaa tactattaag tcacaaacac taacaatttc caactataga ataacagtt    6900 cttatttgga ttttgggaat gctaccaata                                     6930
```

<210> SEQ ID NO 4
<211> LENGTH: 1499
<212> TYPE: PRT
<213> ORGANISM: Homo sapiens

<400> SEQUENCE: 4

```
Met Met Ala Asn Trp Ala Glu Ala Arg Pro Leu Leu Ile Leu Ile Val
 1               5                  10                  15

Leu Leu Gly Gln Phe Val Ser Ile Lys Ala Gln Glu Glu Asp Glu Asp
                20                  25                  30

Glu Gly Tyr Gly Glu Glu Ile Ala Cys Thr Gln Asn Gly Gln Met Tyr
            35                  40                  45

Leu Asn Arg Asp Ile Trp Lys Pro Ala Pro Cys Gln Ile Cys Val Cys
        50                  55                  60

Asp Asn Gly Ala Ile Leu Cys Asp Lys Ile Glu Cys Gln Asp Val Leu
65                  70                  75                  80

Asp Cys Ala Asp Pro Val Thr Pro Pro Gly Glu Cys Cys Pro Val Cys
                85                  90                  95
```

```
Ser Gln Thr Pro Gly Gly Gly Asn Thr Asn Phe Gly Arg Gly Arg Lys
            100                 105                 110

Gly Gln Lys Gly Glu Pro Gly Leu Val Pro Val Val Thr Gly Ile Arg
        115                 120                 125

Gly Arg Pro Gly Pro Ala Gly Pro Pro Gly Ser Gln Gly Pro Arg Gly
    130                 135                 140

Glu Arg Gly Pro Lys Gly Arg Pro Gly Pro Arg Gly Pro Gln Gly Ile
145                 150                 155                 160

Asp Gly Glu Pro Gly Val Pro Gly Gln Pro Gly Ala Pro Gly Pro Pro
                165                 170                 175

Gly His Pro Ser His Pro Gly Pro Asp Gly Leu Ser Arg Pro Phe Ser
                180                 185                 190

Ala Gln Met Ala Gly Leu Asp Glu Lys Ser Gly Leu Gly Ser Gln Val
            195                 200                 205

Gly Leu Met Pro Gly Ser Val Gly Pro Val Gly Pro Arg Gly Pro Gln
        210                 215                 220

Gly Leu Gln Gly Gln Gln Gly Ala Gly Pro Thr Gly Pro Pro Gly
225                 230                 235                 240

Glu Pro Gly Asp Pro Gly Pro Met Gly Pro Ile Gly Ser Arg Gly Pro
                245                 250                 255

Glu Gly Pro Pro Gly Lys Pro Gly Glu Asp Gly Glu Pro Gly Arg Asn
            260                 265                 270

Gly Asn Pro Gly Glu Val Gly Phe Ala Gly Ser Pro Gly Ala Arg Gly
        275                 280                 285

Phe Pro Gly Ala Pro Gly Leu Pro Gly Leu Lys Gly His Arg Gly His
    290                 295                 300

Lys Gly Leu Glu Gly Pro Lys Gly Glu Val Gly Ala Pro Gly Ser Lys
305                 310                 315                 320

Gly Glu Ala Gly Pro Thr Gly Pro Met Gly Ala Met Gly Pro Leu Gly
                325                 330                 335

Pro Arg Gly Met Pro Gly Glu Arg Gly Arg Leu Gly Pro Gln Gly Ala
            340                 345                 350

Pro Gly Gln Arg Gly Ala His Gly Met Pro Gly Lys Pro Gly Pro Met
        355                 360                 365

Gly Pro Leu Gly Ile Pro Gly Ser Ser Gly Phe Pro Gly Asn Pro Gly
    370                 375                 380

Met Lys Gly Glu Ala Gly Pro Thr Gly Ala Arg Gly Pro Glu Gly Pro
385                 390                 395                 400

Gln Gly Gln Arg Gly Glu Thr Gly Pro Pro Gly Pro Val Gly Ser Pro
                405                 410                 415

Gly Leu Pro Gly Ala Ile Gly Thr Asp Gly Thr Pro Gly Ala Lys Gly
            420                 425                 430

Pro Thr Gly Ser Pro Gly Thr Ser Gly Pro Gly Ser Ala Gly Pro
        435                 440                 445

Pro Gly Ser Pro Gly Pro Gln Gly Ser Thr Gly Pro Gln Gly Ile Arg
    450                 455                 460

Gly Gln Pro Gly Asp Pro Gly Val Pro Gly Phe Lys Gly Glu Ala Gly
465                 470                 475                 480

Pro Lys Gly Glu Pro Gly Pro His Gly Ile Gln Gly Pro Ile Gly Pro
                485                 490                 495

Pro Gly Glu Glu Gly Lys Arg Gly Pro Arg Gly Asp Pro Gly Thr Val
            500                 505                 510

Gly Pro Pro Gly Pro Val Gly Glu Arg Gly Ala Pro Gly Asn Arg Gly
```

```
                515                 520                 525
        Phe Pro Gly Ser Asp Gly Leu Pro Gly Pro Lys Gly Ala Gln Gly Glu
            530                 535                 540
        Arg Gly Pro Val Gly Ser Ser Gly Pro Lys Gly Ser Gln Gly Asp Pro
        545                 550                 555                 560
        Gly Arg Pro Gly Glu Pro Gly Leu Pro Gly Ala Arg Gly Leu Thr Gly
                            565                 570                 575
        Asn Pro Gly Val Gln Gly Pro Glu Gly Lys Leu Gly Pro Leu Gly Ala
                        580                 585                 590
        Pro Gly Glu Asp Gly Arg Pro Gly Pro Gly Ser Ile Gly Ile Arg
                    595                 600                 605
        Gly Gln Pro Gly Ser Met Gly Leu Pro Gly Pro Lys Gly Ser Ser Gly
                610                 615                 620
        Asp Pro Gly Lys Pro Gly Glu Ala Gly Asn Ala Gly Val Pro Gly Gln
        625                 630                 635                 640
        Arg Gly Ala Pro Gly Lys Asp Gly Glu Val Gly Pro Ser Gly Pro Val
                            645                 650                 655
        Gly Pro Pro Gly Leu Ala Gly Glu Arg Gly Glu Gln Gly Pro Pro Gly
                        660                 665                 670
        Pro Thr Gly Phe Gln Gly Leu Pro Gly Pro Gly Pro Pro Gly Glu
                    675                 680                 685
        Gly Gly Lys Pro Gly Asp Gln Gly Val Pro Gly Asp Pro Gly Ala Val
                690                 695                 700
        Gly Pro Leu Gly Pro Arg Gly Glu Arg Gly Asn Pro Gly Glu Arg Gly
        705                 710                 715                 720
        Glu Pro Gly Ile Thr Gly Leu Pro Gly Glu Lys Gly Met Ala Gly Gly
                            725                 730                 735
        His Gly Pro Asp Gly Pro Lys Gly Ser Pro Gly Pro Ser Gly Thr Pro
                        740                 745                 750
        Gly Asp Thr Gly Pro Pro Gly Leu Gln Gly Met Pro Gly Glu Arg Gly
                    755                 760                 765
        Ile Ala Gly Thr Pro Gly Pro Lys Gly Asp Arg Gly Gly Ile Gly Glu
                770                 775                 780
        Lys Gly Ala Glu Gly Thr Ala Gly Asn Asp Gly Ala Arg Gly Leu Pro
        785                 790                 795                 800
        Gly Pro Leu Gly Pro Pro Gly Ala Pro Gly Thr Gly Glu Lys Gly
                            805                 810                 815
        Glu Pro Gly Pro Arg Gly Leu Val Gly Pro Pro Gly Ser Arg Gly Asn
                        820                 825                 830
        Pro Gly Ser Arg Gly Glu Asn Gly Pro Thr Gly Ala Val Gly Phe Ala
                    835                 840                 845
        Gly Pro Gln Gly Pro Asp Gly Gln Pro Gly Val Lys Gly Glu Pro Gly
                850                 855                 860
        Glu Pro Gly Gln Lys Gly Asp Ala Gly Ser Pro Gly Pro Gln Gly Leu
        865                 870                 875                 880
        Ala Gly Ser Pro Gly Pro His Gly Pro Asn Gly Val Pro Gly Leu Lys
                            885                 890                 895
        Gly Gly Arg Gly Thr Gln Gly Pro Pro Gly Ala Thr Gly Phe Pro Gly
                        900                 905                 910
        Ser Ala Gly Arg Val Gly Pro Pro Gly Pro Ala Gly Pro Gly Pro
                    915                 920                 925
        Ala Gly Pro Leu Gly Glu Pro Gly Lys Glu Gly Pro Pro Gly Leu Arg
                930                 935                 940
```

```
Gly Asp Pro Gly Ser His Gly Arg Val Gly Asp Arg Gly Pro Ala Gly
945                 950                 955                 960

Pro Pro Gly Gly Pro Gly Asp Lys Gly Asp Pro Gly Glu Asp Gly Gln
            965                 970                 975

Pro Gly Pro Asp Gly Pro Pro Gly Pro Ala Gly Thr Thr Gly Gln Arg
        980                 985                 990

Gly Ile Val Gly Met Pro Gly Gln Arg Gly Glu Arg Gly Met Pro Gly
    995                 1000                1005

Leu Pro Gly Pro Ala Gly Thr Pro Gly Lys Val Gly Pro Thr Gly Ala
1010                1015                1020

Thr Gly Asp Lys Gly Pro Pro Gly Pro Val Gly Pro Gly Ser Asn
1025                1030                1035                1040

Gly Pro Val Gly Glu Pro Gly Pro Glu Gly Pro Ala Gly Asn Asp Gly
                1045                1050                1055

Thr Pro Gly Arg Asp Gly Ala Val Gly Glu Arg Gly Asp Arg Gly Asp
                1060                1065                1070

Pro Gly Pro Ala Gly Leu Pro Gly Ser Gln Gly Ala Pro Gly Thr Pro
            1075                1080                1085

Gly Pro Val Gly Ala Pro Gly Asp Ala Gly Gln Arg Gly Asp Pro Gly
1090                1095                1100

Ser Arg Gly Pro Ile Gly Pro Pro Gly Arg Ala Gly Lys Arg Gly Leu
1105                1110                1115                1120

Pro Gly Pro Gln Gly Pro Arg Gly Asp Lys Gly Asp His Gly Asp Arg
            1125                1130                1135

Gly Asp Arg Gly Gln Lys Gly His Arg Gly Phe Thr Gly Leu Gln Gly
            1140                1145                1150

Leu Pro Gly Pro Pro Gly Pro Asn Gly Glu Gln Gly Ser Ala Gly Ile
            1155                1160                1165

Pro Gly Pro Phe Gly Pro Arg Gly Pro Pro Gly Pro Val Gly Pro Ser
            1170                1175                1180

Gly Lys Glu Gly Asn Pro Gly Pro Leu Gly Pro Ile Gly Pro Pro Gly
1185                1190                1195                1200

Val Arg Gly Ser Val Gly Glu Ala Gly Pro Glu Gly Pro Pro Gly Glu
            1205                1210                1215

Pro Gly Pro Pro Gly Pro Pro Gly Pro Pro Gly His Leu Thr Ala Ala
            1220                1225                1230

Leu Gly Asp Ile Met Gly His Tyr Asp Glu Ser Met Pro Asp Pro Leu
            1235                1240                1245

Pro Glu Phe Thr Glu Asp Gln Ala Ala Pro Asp Asp Lys Asn Lys Thr
            1250                1255                1260

Asp Pro Gly Val His Ala Thr Leu Lys Ser Leu Ser Ser Gln Ile Glu
1265                1270                1275                1280

Thr Met Arg Ser Pro Asp Gly Ser Lys Lys His Pro Ala Arg Thr Cys
            1285                1290                1295

Asp Asp Leu Lys Leu Cys His Ser Ala Lys Gln Ser Gly Glu Tyr Trp
            1300                1305                1310

Ile Asp Pro Asn Gln Gly Ser Val Glu Asp Ala Ile Lys Val Tyr Cys
            1315                1320                1325

Asn Met Glu Thr Gly Glu Thr Cys Ile Ser Ala Asn Pro Ser Ser Val
            1330                1335                1340

Pro Arg Lys Thr Trp Trp Ala Ser Lys Ser Pro Asp Asn Lys Pro Val
1345                1350                1355                1360

Trp Tyr Gly Leu Asp Met Asn Arg Gly Ser Gln Phe Ala Tyr Gly Asp
            1365                1370                1375
```

```
His Gln Ser Pro Asn Thr Ala Ile Thr Gln Met Thr Phe Leu Arg Leu
        1380                1385                1390

Leu Ser Lys Glu Ala Ser Gln Asn Ile Thr Tyr Ile Cys Lys Asn Ser
    1395                1400                1405

Val Gly Tyr Met Asp Asp Gln Ala Lys Asn Leu Lys Lys Ala Val Val
    1410                1415                1420

Leu Lys Gly Ala Asn Asp Leu Asp Ile Lys Ala Glu Gly Asn Ile Arg
1425                1430                1435                1440

Phe Arg Tyr Ile Val Leu Gln Asp Thr Cys Ser Lys Arg Asn Gly Asn
            1445                1450                1455

Val Gly Lys Thr Val Phe Glu Tyr Arg Thr Gln Asn Val Ala Arg Leu
        1460                1465                1470

Pro Ile Ile Asp Leu Ala Pro Val Asp Val Gly Gly Thr Asp Gln Glu
    1475                1480                1485

Phe Gly Val Glu Ile Gly Pro Val Cys Phe Val
    1490                1495

<210> SEQ ID NO 5
<211> LENGTH: 6192
<212> TYPE: DNA
<213> ORGANISM: Homo sapiens

<400> SEQUENCE: 5
gcgagtgact gcaccgagcc cgagaagtcg ccgcgccccg cagccgcccc gactggttcc      60
ccgccttgcc cgtgggcccc gccgggatgg ggaaccgccg ggacctgggc cagccgcggg     120
ccggtctctg cctgctcctg gccgcgctgc agcttctgcc ggggacgcag gccgatcctg     180
tggatgtcct gaaggccctg ggtgtgcagg aggccaggc tggggtcccc gaggggcctg     240
gcttctgtcc ccagaggact ccagagggtg accgggcatt cagaattggc caggccagca     300
cgctcggcat ccccacgtgg gaactctttc cagaaggcca cttttcctga aacttctcct     360
tgctgatcac cttgcgggga cagccagcca atcagtctgt cctgctgtcc atttatgatg     420 aaagggggtgc ccggcagttg ggcctggcac tgggccagc gctgggtctc ctaggtgacc     480
ccttccgccc cctccccag caggtcaacc tcacagatgg caggtggcac cgtgtggccg     540
tcagcataga tggtgagatg gtgaccctgg tagctgactg tgaagctcag ccccctgttt     600
tgggccatgg ccccgcttc atcagcatag ctggactcac tgtgctgggg acccaggacc     660
ttggggaaaa gactttcgag ggagacattc aggagctgct gataagccca gatcctcagg     720
ctgccttcca ggcttgtgag cggtacctcc ccgactgtga caacctggca ccggcagcca     780
cagtggctcc ccagggtgaa ccagaaaccc ctcgtcctcg gcggaagggg aagggaaaag     840
ggaggaagaa agggcgaggt cgcaagggga agggcaggaa aaagaacaag gaaatttgga     900
cctcaagtcc acctcctgac tccgcagaga accagacctc cactgacatc cccaagacag     960
agactccagc tccaaatctg cctccgaccc ccacgccttt ggtcgtcacc tccactgtga    1020
ctactggact caatgccacg atcctagaga ggagcttgga ccctgacagt ggaaccgagc    1080
tggggacccc ggagaccaag gcagccaggg aggatgaaga aggagatgat ccaccatgg    1140 gccctgactt ccgggcagca gaatatccat ctcggactca gttccagatc tttcctggtg    1200
ctggagagaa aggagcaaaa ggagagcccc agtgattga aaaggggcag cagtttgagg    1260
gacctccagg agcccagga ccccaagggg tggttggccc ctcaggccct ccggccccc    1320 caggattccc tggcgaccct ggtccaccgg gccctgctgg cctcccagga atccccggca    1380
ttgatgggat ccgaggccca ccgggcactg tgatcatgat gccgttccag tttgcaggcg    1440
```

```
gctcctttaa aggcccccca gtctcattcc agcaggccca ggctcaggca gttctgcagc    1500
agactcagct ctctatgaaa ggccccctg gtccagtggg gctcactggg cgcccaggcc    1560
ctgtgggtct ccccgggcat ccaggtctga aggagagga gggagcagaa gggccacagg    1620
gtccccgagg cctgcaggga cctcatggac cccctggccg agtgggcaag atgggccgcc    1680
ctggagcaga tggagctcgg ggcctcccag gggacactgg acctaagggt gatcgtggct    1740
tcgatggcct ccctgggctg cctggtgaga agggccaaag gggtgacttt ggccatgtgg    1800
ggcaacccgg tcccccagga gaggatggtg agagggagc agagggacct ccagggccca    1860
ctggccaggc tggggagccg ggtccacgag gactgcttgg ccccagaggc tctcctggcc    1920
ccacgggtcg cccgggtgtg actggaattg atggtgctcc tggtgccaaa ggcaatgtgg    1980
gtcctccagg agaaccaggc cctccgggac agcaggaaa ccatgggtcc caggactcc    2040 ccggtcccca gggactcatt ggcactcctg gggagaaggg tccccctgga aacccaggaa    2100
ttccaggcct cccaggatcc gatggccctc tgggtcaccc aggacatgag gccccacgg    2160 gagagaaagg ggctcagggt ccaccagggt cggcaggccc tccgggctat cctggacctc    2220
ggggagtgaa gggcacttca ggcaaccggg gcctccaggg ggagaaaggc gagaagggag    2280
aggacggctt cccaggcttc aagggcgatg tggggctcaa aggtgatcag gggaaacccg    2340
gagctccagg tccccgggga gaggatggtc ctgaggggcc gaaggggcag gcggggcagg    2400
ctggcgagga ggggccccca ggctcagctg gggagaaggg caagcttggg gtgccaggcc    2460
tcccaggtta tccaggacgc cctggaccta agggatctat tggatttccc ggtcccctgg    2520
gacccatagg agagaaaggg aagtcgggaa agacagggca gccaggcctg aaggagagc    2580 ggggaccacc aggttcccgt ggagagaggg ggcaaccggg tgccacaggg caaccaggcc    2640
ccaagggcga tgtgggccag gatggagccc ctgggatccc tggagaaaag ggcctccctg    2700
gtctgcaagg ccctccagga ttccctgggc caaaggcccc cctggtcac caaggtaaag    2760 atgggcgacc agggcaccct ggacagagag gagaactggg cttccaaggt cagacaggcc    2820
cgcctggacc agctggtgtc ttaggccctc agggaaagac aggagaagtg ggacctctag    2880
gtgaaagggg gcctccaggc cccctggac ctcctggtga acaaggtctt cctggcctgg    2940
aaggcagaga gggggccaag ggggaactgg gaccaccagg accccttggg aaagaagggc    3000
cagctggact caggggcttt ccggccccca agggggccc tggggacccg ggacctactg    3060
gcttaaaggg tgataagggc ccccagggc ccgtggggc caatggctcc cctggtgagc    3120
gcggtccttt gggcccagca ggaggcattg gacttcctgg ccaaagtggc agcgaaggcc    3180
ccgttggccc tgcaggcaag aagggtccc ggggagaacg tggccccct ggccccactg    3240 gcaaagatgg gatcccaggg cccctggggc ctctgggacc cctggagct gctgggcctt    3300 ctggcgagga aggacaag gggatgtgg gtgcccccgg acacaagggg agtaaaggcg    3360
ataaaggaga cgcgggccca cctggacaac cagggatacg gggtcctgca ggacacccag    3420 gtccccgg agcagacggg gctcaggggc gccgggacc cccaggcctc tttgggcaga    3480
aaggagatga cggagtcaga ggctttgtgg gggtgattgg ccctcctgga ctgcaggggc    3540
tgccaggccc tccgggagag aaaggggag tcggagacgt cgggtccatg ggtccccatg    3600
gagctccagg tcctcggggt ccccaaggcc ccactggatc agagggcact ccagggctgc    3660
ctggaggagt tggtcagcca ggcgccgtgg gtgagaaggg tgagcgaggg gacgctggag    3720
acccagggcc tccaggagcc ccaggcatcc cgggcccaa gggagacatt ggtgaaaagg    3780
gggactcagg cccatctgga gctgctggac ccccaggcaa gaaaggtccc cctggagagg    3840
```

```
atggagccaa agggagcgtg ggccccacgg ggctgcccgg agatctaggg ccccaggag    3900
accctggagt ttcaggcata gatggttccc caggggagaa gggagaccct ggtgatgttg    3960
ggggaccggg tccgcctgga gcttctgggg agcccggcgc cccgggccc cccggcaaga    4020
ggggtccttc aggccacatg ggtcgagaag gcagagaagg ggagaaaggt gccaaggggg    4080
agccaggtcc tgatgggccc ccagggagga cgggtccaat gggggctaga ggccccctg    4140
gacgtgtggg gcctgagggt cttcgaggga tccctggccc tgtgggtgaa ccaggcctcc    4200
tgggagcccc tggacagatg ggccctcctg gcccctggg gccctctggc ctcccagggc    4260
tgaagggaga cactggcccc aaggggga aagggccacat tggattgatc ggtctcattg    4320
gccccccggg agaagctggt gagaaaggag atcaggggtt gccaggcgtg cagggacccc    4380
ctggtcccaa gggagaccct ggtccccctg gtcccattgg ctctctgggc caccctgggc    4440
ccccaggtgt ggcgggccct ctaggacaga aaggctcaaa agggtctccg gggtccatgg    4500
gccccgtgg agacactgga cctgcaggcc caccaggccc cccgggtgcc cctgccgagc    4560
tgcatgggct gcgcaggcgc cggcgcttcg tcccagtccc gcttccagtc gtggagggcg    4620
gcctggagga ggtgctggcc tcgctcacat cgctgagctt ggagctggag cagctgcggc    4680
gtcctcccgg cactgcggag cgcccgggcc tcgtgtgcca cgagctgcac cgcaaccacc    4740
cgcacctgcc tgatggggaa tactggattg accccaacca gggctgcgcg cgggactcgt    4800
tcagggtttt ttgcaacttc acggcgggag gagagacctg cctctatccc gacaagaagt    4860
ttgagatcgt gaaattggcc tcctggtcca aggaaaagcc tggaggctgg tatagcacat    4920
tccgtcgagg gaagaagttc tcctacgtgg acgccgacgg gtccccagtg aatgtcgtgc    4980
agctgaactt cctgaaactg ctgagtgcca cagctcgcca gaacttcacc tactcctgcc    5040
agaatgcagc tgcctggctg gacgaagcca cgggtgacta cagccactcc gcccgcttcc    5100
ttggcaccaa tggagaggag ctgtctttca ccagacgac agcagccact gtcagcgtcc    5160
cccaggatgg ctgccggctc cggaaaggac agacgaagac ccttttcgaa ttcagctctt    5220
ctcgagcggg atttctgccc ctgtgggatg tggcggccac tgactttggc cagacgaacc    5280
aaaagtttgg gtttgaactg ggccccgtct gcttcagcag ctgagagtgt ccggggtggg    5340
agggaccatg agggagcccc agaatggggt gcatttggtg ctgaggcttt gaagccaccg    5400
tatttttcgt tacctgtgac tatggagcca atgggatgtg acttcgctca tcacggacag    5460
tcattccttc tccttttccag ggtgctgggg gctgggggttc cctggcccaa gggtccagcc    5520
tcctctcacc ccattccagg tggcatactg cagtctggct cttttctcccc tccctcccca    5580
cccaagcctc acctcccccac cccttgaacc cccatgcaat gagcttctaa ctcagagctg    5640
atgaacaaaa gccccccac ccccaatgcc tgcctcctca ctcctccgtc gctgcccttc    5700
acaccttttg gtgctacccc tccccagagt taagcactgg atgtctcctg atcccaggct    5760
gggaccccta cccccacccc ctttgatcct ttctacttcc acgtgaaag gactgaggtc    5820
ggactacaga gggaagaggg acttcccttg actgggttgt gtttcttttc ctgcctcagc    5880
ccagctctgc aaatccccctc cccctgcccc ccacctcccc aggctcacct tgccatgcca    5940
ggtggtttgg ggaccaagat gttgggggg tgaatcagga tcctaatggt gctgccctat    6000
ttatacctgg gtctgtatta aaaggggaaag tccccccctgt gtagatttc atctgcttcc    6060
tccttaggga aggctgggat atgatgagag attccagccc aagcctggcc ccccaccgcc    6120
aggccatagg gcataatttg catctcaaat ctgagaataa actgatgaac tgtgaaaaaa    6180
aaaaaaaaaa aa                                                        6192
```

<210> SEQ ID NO 6
<211> LENGTH: 1745
<212> TYPE: PRT
<213> ORGANISM: Homo sapiens

<400> SEQUENCE: 6

```
Met Gly Asn Arg Arg Asp Leu Gly Gln Pro Arg Ala Gly Leu Cys Leu
 1               5                   10                  15

Leu Leu Ala Ala Leu Gln Leu Leu Pro Gly Thr Gln Ala Asp Pro Val
            20                  25                  30

Asp Val Leu Lys Ala Leu Gly Val Gln Gly Gln Ala Gly Val Pro
        35                  40                  45

Glu Gly Pro Gly Phe Cys Pro Gln Arg Thr Pro Glu Gly Asp Arg Ala
 50                  55                  60

Phe Arg Ile Gly Gln Ala Ser Thr Leu Gly Ile Pro Thr Trp Glu Leu
 65                  70                  75                  80

Phe Pro Glu Gly His Phe Pro Glu Asn Phe Ser Leu Leu Ile Thr Leu
                85                  90                  95

Arg Gly Gln Pro Ala Asn Gln Ser Val Leu Leu Ser Ile Tyr Asp Glu
            100                 105                 110

Arg Gly Ala Arg Gln Leu Gly Leu Ala Leu Gly Pro Ala Leu Gly Leu
        115                 120                 125

Leu Gly Asp Pro Phe Arg Pro Leu Pro Gln Gln Val Asn Leu Thr Asp
130                 135                 140

Gly Arg Trp His Arg Val Ala Val Ser Ile Asp Gly Glu Met Val Thr
145                 150                 155                 160

Leu Val Ala Asp Cys Glu Ala Gln Pro Val Leu Gly His Gly Pro
                165                 170                 175

Arg Phe Ile Ser Ile Ala Gly Leu Thr Val Leu Gly Thr Gln Asp Leu
            180                 185                 190

Gly Glu Lys Thr Phe Glu Gly Asp Ile Gln Glu Leu Leu Ile Ser Pro
        195                 200                 205

Asp Pro Gln Ala Ala Phe Gln Ala Cys Glu Arg Tyr Leu Pro Asp Cys
    210                 215                 220

Asp Asn Leu Ala Pro Ala Ala Thr Val Ala Pro Gln Gly Glu Pro Glu
225                 230                 235                 240

Thr Pro Arg Pro Arg Arg Lys Gly Lys Gly Lys Gly Arg Lys Lys Gly
                245                 250                 255

Arg Gly Arg Lys Gly Lys Gly Arg Lys Lys Asn Lys Glu Ile Trp Thr
            260                 265                 270

Ser Ser Pro Pro Pro Asp Ser Ala Glu Asn Gln Thr Ser Thr Asp Ile
        275                 280                 285

Pro Lys Thr Glu Thr Pro Ala Pro Asn Leu Pro Thr Pro Thr Pro
    290                 295                 300

Leu Val Val Thr Ser Thr Val Thr Thr Gly Leu Asn Ala Thr Ile Leu
305                 310                 315                 320

Glu Arg Ser Leu Asp Pro Asp Ser Gly Thr Glu Leu Gly Thr Leu Glu
                325                 330                 335

Thr Lys Ala Ala Arg Glu Asp Glu Glu Gly Asp Asp Ser Thr Met Gly
            340                 345                 350

Pro Asp Phe Arg Ala Ala Glu Tyr Pro Ser Arg Thr Gln Phe Gln Ile
        355                 360                 365

Phe Pro Gly Ala Gly Glu Lys Gly Ala Lys Gly Glu Pro Ala Val Ile
    370                 375                 380
```

```
Glu Lys Gly Gln Gln Phe Glu Gly Pro Pro Gly Ala Pro Gly Pro Gln
385                 390                 395                 400

Gly Val Val Gly Pro Ser Gly Pro Pro Gly Pro Gly Phe Pro Gly
            405                 410                 415

Asp Pro Gly Pro Pro Gly Pro Ala Gly Leu Pro Gly Ile Pro Gly Ile
            420                 425                 430

Asp Gly Ile Arg Gly Pro Pro Gly Thr Val Ile Met Met Pro Phe Gln
            435                 440                 445

Phe Ala Gly Gly Ser Phe Lys Gly Pro Pro Val Ser Phe Gln Gln Ala
            450                 455                 460

Gln Ala Gln Ala Val Leu Gln Gln Thr Gln Leu Ser Met Lys Gly Pro
465                 470                 475                 480

Pro Gly Pro Val Gly Leu Thr Gly Arg Pro Gly Pro Val Gly Leu Pro
                485                 490                 495

Gly His Pro Gly Leu Lys Gly Glu Glu Gly Ala Glu Gly Pro Gln Gly
            500                 505                 510

Pro Arg Gly Leu Gln Gly Pro His Gly Pro Pro Gly Arg Val Gly Lys
            515                 520                 525

Met Gly Arg Pro Gly Ala Asp Gly Ala Arg Gly Leu Pro Gly Asp Thr
530                 535                 540

Gly Pro Lys Gly Asp Arg Gly Phe Asp Gly Leu Pro Gly Leu Pro Gly
545                 550                 555                 560

Glu Lys Gly Gln Arg Gly Asp Phe Gly His Val Gly Gln Pro Gly Pro
                565                 570                 575

Pro Gly Glu Asp Gly Glu Arg Gly Ala Glu Gly Pro Pro Gly Pro Thr
            580                 585                 590

Gly Gln Ala Gly Glu Pro Gly Pro Arg Gly Leu Leu Gly Pro Arg Gly
            595                 600                 605

Ser Pro Gly Pro Thr Gly Arg Pro Gly Val Thr Gly Ile Asp Gly Ala
610                 615                 620

Pro Gly Ala Lys Gly Asn Val Gly Pro Pro Gly Glu Pro Gly Pro Pro
625                 630                 635                 640

Gly Gln Gln Gly Asn His Gly Ser Gln Gly Leu Pro Gly Pro Gln Gly
            645                 650                 655

Leu Ile Gly Thr Pro Gly Glu Lys Gly Pro Pro Gly Asn Pro Gly Ile
            660                 665                 670

Pro Gly Leu Pro Gly Ser Asp Gly Pro Leu Gly His Pro Gly His Glu
            675                 680                 685

Gly Pro Thr Gly Glu Lys Gly Ala Gln Gly Pro Pro Gly Ser Ala Gly
            690                 695                 700

Pro Pro Gly Tyr Pro Gly Pro Arg Gly Val Lys Gly Thr Ser Gly Asn
705                 710                 715                 720

Arg Gly Leu Gln Gly Glu Lys Gly Glu Lys Gly Glu Asp Gly Phe Pro
            725                 730                 735

Gly Phe Lys Gly Asp Val Gly Leu Lys Gly Asp Gln Gly Lys Pro Gly
            740                 745                 750

Ala Pro Gly Pro Arg Gly Glu Asp Gly Pro Glu Gly Pro Lys Gly Gln
            755                 760                 765

Ala Gly Gln Ala Gly Glu Glu Gly Pro Pro Gly Ser Ala Gly Glu Lys
            770                 775                 780

Gly Lys Leu Gly Val Pro Gly Leu Pro Gly Tyr Pro Gly Arg Pro Gly
785                 790                 795                 800

Pro Lys Gly Ser Ile Gly Phe Pro Gly Pro Leu Gly Pro Ile Gly Glu
```

-continued

```
                805                 810                 815
Lys Gly Lys Ser Gly Lys Thr Gly Gln Pro Gly Leu Glu Gly Glu Arg
            820                 825                 830

Gly Pro Pro Gly Ser Arg Gly Glu Arg Gly Gln Pro Gly Ala Thr Gly
            835                 840                 845

Gln Pro Gly Pro Lys Gly Asp Val Gly Gln Asp Gly Ala Pro Gly Ile
850                 855                 860

Pro Gly Glu Lys Gly Leu Pro Gly Leu Gln Gly Pro Gly Phe Pro
865                 870                 875                 880

Gly Pro Lys Gly Pro Gly His Gln Gly Lys Asp Gly Arg Pro Gly
            885                 890                 895

His Pro Gly Gln Arg Gly Glu Leu Gly Phe Gln Gly Gln Thr Gly Pro
            900                 905                 910

Pro Gly Pro Ala Gly Val Leu Gly Pro Gln Gly Lys Thr Gly Glu Val
            915                 920                 925

Gly Pro Leu Gly Glu Arg Gly Pro Pro Gly Pro Gly Pro Pro Gly
            930                 935                 940

Glu Gln Gly Leu Pro Gly Leu Glu Gly Arg Glu Gly Ala Lys Gly Glu
945                 950                 955                 960

Leu Gly Pro Pro Gly Pro Leu Gly Lys Glu Gly Pro Ala Gly Leu Arg
            965                 970                 975

Gly Phe Pro Gly Pro Lys Gly Gly Pro Gly Asp Pro Gly Pro Thr Gly
            980                 985                 990

Leu Lys Gly Asp Lys Gly Pro Pro Gly Pro Val Gly Ala Asn Gly Ser
            995                 1000                1005

Pro Gly Glu Arg Gly Pro Leu Gly Pro Ala Gly Gly Ile Gly Leu Pro
    1010                1015                1020

Gly Gln Ser Gly Ser Glu Gly Pro Val Gly Pro Ala Gly Lys Lys Gly
    1025                1030                1035                1040

Ser Arg Gly Glu Arg Gly Pro Pro Gly Pro Thr Gly Lys Asp Gly Ile
                1045                1050                1055

Pro Gly Pro Leu Gly Pro Leu Gly Pro Pro Gly Ala Ala Gly Pro Ser
                1060                1065                1070

Gly Glu Glu Gly Asp Lys Gly Asp Val Gly Ala Pro Gly His Lys Gly
                1075                1080                1085

Ser Lys Gly Asp Lys Gly Asp Ala Gly Pro Pro Gly Gln Pro Gly Ile
                1090                1095                1100

Arg Gly Pro Ala Gly His Pro Gly Pro Pro Gly Ala Asp Gly Ala Gln
1105                1110                1115                1120

Gly Arg Arg Gly Pro Pro Gly Leu Phe Gly Gln Lys Gly Asp Asp Gly
                1125                1130                1135

Val Arg Gly Phe Val Gly Val Ile Gly Pro Pro Gly Leu Gln Gly Leu
                1140                1145                1150

Pro Gly Pro Pro Gly Glu Lys Gly Glu Val Gly Asp Val Gly Ser Met
                1155                1160                1165

Gly Pro His Gly Ala Pro Gly Pro Arg Gly Pro Gln Gly Pro Thr Gly
                1170                1175                1180

Ser Glu Gly Thr Pro Gly Leu Pro Gly Val Gly Gln Pro Gly Ala
1185                1190                1195                1200

Val Gly Glu Lys Gly Glu Arg Gly Asp Ala Gly Asp Pro Gly Pro Pro
                1205                1210                1215

Gly Ala Pro Gly Ile Pro Gly Pro Lys Gly Asp Ile Gly Glu Lys Gly
                1220                1225                1230
```

-continued

Asp Ser Gly Pro Ser Gly Ala Ala Gly Pro Pro Gly Lys Lys Gly Pro
              1235                1240                1245

Pro Gly Glu Asp Gly Ala Lys Gly Ser Val Gly Pro Thr Gly Leu Pro
    1250                1255                1260

Gly Asp Leu Gly Pro Pro Gly Asp Pro Gly Val Ser Gly Ile Asp Gly
1265                1270                1275                1280

Ser Pro Gly Glu Lys Gly Asp Pro Gly Asp Val Gly Pro Gly Pro
              1285                1290                1295

Pro Gly Ala Ser Gly Glu Pro Gly Ala Pro Gly Pro Gly Lys Arg
              1300                1305                1310

Gly Pro Ser Gly His Met Gly Arg Glu Gly Arg Glu Gly Glu Lys Gly
              1315                1320                1325

Ala Lys Gly Glu Pro Gly Pro Asp Gly Pro Pro Gly Arg Thr Gly Pro
              1330                1335                1340

Met Gly Ala Arg Gly Pro Pro Gly Arg Val Gly Pro Glu Gly Leu Arg
1345                1350                1355                1360

Gly Ile Pro Gly Pro Val Gly Glu Pro Gly Leu Leu Gly Ala Pro Gly
              1365                1370                1375

Gln Met Gly Pro Pro Gly Pro Leu Gly Pro Ser Gly Leu Pro Gly Leu
              1380                1385                1390

Lys Gly Asp Thr Gly Pro Lys Gly Glu Lys Gly His Ile Gly Leu Ile
              1395                1400                1405

Gly Leu Ile Gly Pro Pro Gly Glu Ala Gly Glu Lys Gly Asp Gln Gly
              1410                1415                1420

Leu Pro Gly Val Gln Gly Pro Pro Gly Pro Lys Gly Asp Pro Gly Pro
1425                1430                1435                1440

Pro Gly Pro Ile Gly Ser Leu Gly His Pro Gly Pro Pro Gly Val Ala
              1445                1450                1455

Gly Pro Leu Gly Gln Lys Gly Ser Lys Gly Ser Pro Gly Ser Met Gly
              1460                1465                1470

Pro Arg Gly Asp Thr Gly Pro Ala Gly Pro Pro Gly Pro Pro Gly Ala
              1475                1480                1485

Pro Ala Glu Leu His Gly Leu Arg Arg Arg Arg Phe Val Pro Val
              1490                1495                1500

Pro Leu Pro Val Val Glu Gly Gly Leu Glu Glu Val Leu Ala Ser Leu
1505                1510                1515                1520

Thr Ser Leu Ser Leu Glu Leu Glu Gln Leu Arg Arg Pro Pro Gly Thr
              1525                1530                1535

Ala Glu Arg Pro Gly Leu Val Cys His Glu Leu His Arg Asn His Pro
              1540                1545                1550

His Leu Pro Asp Gly Glu Tyr Trp Ile Asp Pro Asn Gln Gly Cys Ala
              1555                1560                1565

Arg Asp Ser Phe Arg Val Phe Cys Asn Phe Thr Ala Gly Gly Glu Thr
              1570                1575                1580

Cys Leu Tyr Pro Asp Lys Lys Phe Glu Ile Val Lys Leu Ala Ser Trp
1585                1590                1595                1600

Ser Lys Glu Lys Pro Gly Gly Trp Tyr Ser Thr Phe Arg Gly Lys
              1605                1610                1615

Lys Phe Ser Tyr Val Asp Ala Asp Gly Ser Pro Val Asn Val Val Gln
              1620                1625                1630

Leu Asn Phe Leu Lys Leu Leu Ser Ala Thr Ala Arg Gln Asn Phe Thr
              1635                1640                1645

Tyr Ser Cys Gln Asn Ala Ala Ala Trp Leu Asp Glu Ala Thr Gly Asp
              1650                1655                1660

-continued

```
Tyr Ser His Ser Ala Arg Phe Leu Gly Thr Asn Gly Glu Glu Leu Ser
1665                1670                1675                1680

Phe Asn Gln Thr Thr Ala Ala Thr Val Ser Val Pro Gln Asp Gly Cys
            1685                1690                1695

Arg Leu Arg Lys Gly Gln Thr Lys Thr Leu Phe Glu Phe Ser Ser Ser
            1700            1705                1710

Arg Ala Gly Phe Leu Pro Leu Trp Asp Val Ala Ala Thr Asp Phe Gly
        1715                1720                1725

Gln Thr Asn Gln Lys Phe Gly Phe Glu Leu Gly Pro Val Cys Phe Ser
        1730            1735                1740

Ser
1745
```

COMPOSITIONS FOR USE IN THE TREATMENT OF CHRONIC OBSTRUCTIVE PULMONARY DISEASES AND ASTHMA

CROSS-REFERENCE TO RELATED APPLICATIONS

This is a U.S. national phase application of International PCT Patent Application No. PCT/US2010/032007, which was filed on Apr. 22, 2010, which claims the benefit under 35 U.S.C. 119(e) of U.S. Provisional Patent Application No. 61/171,705, filed Apr. 22, 2009, and U.S. Provisional Patent Application No. 61/266,048 filed Dec. 2, 2009, which are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is IURT_004_02US_ST25.txt. The text file is 67 KB, was created on Sep. 10, 2012, and is being submitted electronically via EFS-Web.

BACKGROUND OF THE INVENTION

1. Field of the Invention

The present invention relates to methods for the treatment of chronic obstructive pulmonary disease (COPD) and asthma. In particular the invention relates to the treatment of COPD and asthma by administering type V Collagen (colV) or tolerogenic fragments thereof.

2. Description of the Related Art

Chronic obstructive pulmonary disease (COPD) is a group of diseases of the lungs in which the airways become narrowed. This leads to a limitation of the flow of air to and from the lungs causing shortness of breath. In contrast to asthma, the limitation of airflow is poorly reversible and usually gets progressively worse over time. COPD is also known as chronic obstructive lung disease (COLD), chronic obstructive airway disease (COAD), chronic airflow limitation (CAL) and chronic obstructive respiratory disease. The term "COPD" includes two main conditions—emphysema and chronic obstructive bronchitis.

In emphysema, the walls between many of the air sacs are damaged, causing them to lose their shape and become floppy. This damage also can destroy the walls of the air sacs, leading to fewer and larger air sacs instead of many tiny ones.

In chronic obstructive bronchitis, the lining of the airways is constantly irritated and inflamed. This causes the lining to thicken. Lots of thick mucus forms in the airways, making it hard to breathe.

Most people who have COPD have both emphysema and chronic obstructive bronchitis. Thus, the general term "COPD" is more accurate.

Chronic bronchitis and emphysema are most commonly caused by smoking; approximately 90% of patients with COPD are or were smokers. Although approximately 50% of smokers develop chronic bronchitis, only 15% of smokers develop disabling airflow obstruction. Certain other mammals, particularly horses, suffer from COPD as well.

The airflow obstruction associated with COPD is progressive, may be accompanied by airway hyperreactivity, and may be partially reversible. Non-specific airway hyper-responsiveness may also play a role in the development of COPD and may be predictive of an accelerated rate of decline in lung function in smokers.

COPD is a significant cause of death and disability. It is currently the fourth leading cause of death in the United States and Europe. Treatment guidelines advocate early detection and implementation of smoking cessation programs to help reduce morbidity and mortality due to the disease. However, early detection and diagnosis has been difficult for a number of reasons.

COPD takes years to develop and smokers often deny any ill effects from smoking, attributing the early warning signs of increased breathlessness as a sign of age. Similarly, acute episodes of bronchitis often are not recognized by the general practitioner as early signs of COPD. Many patients exhibit features of more than one disease (e.g. chronic bronchitis or asthmatic bronchitis) making precise diagnosis a challenge, particularly in early disease. Also, many patients do not seek medical help until they are experiencing more severe symptoms associated with reduced lung function, such as dyspnea, persistent cough, and sputum production. As a consequence, the vast majority of patients are not diagnosed or treated until they are in a more advanced stage of disease.

Asthma is a heterogeneous disorder of the airways that afflicts millions of people. Airway inflammation, hyperresponsiveness, and obstruction characterize the condition. The disease often causes spasms of the bronchial smooth muscle system, and affects both the upper and lower respiratory tracts. There are several forms of asthma, characterized by varying degrees of severity. Mild asthma, for example, is defined as brief episodes of wheezing, with or without dyspnea or cough. Moderately severe asthma is defined as wheezing and dyspnea, and can be with or without cough and expectoration, but generally interferes with daily activities and/or sleeping. Severe asthma is characterized by incapacitation due to dyspnea, and the afflicted patient typically is unable to eat or sleep normally, is very anxious, and is often exhausted. A condition known as status asthmaticus is the most severe form of asthma, and generally requires intensive hospital care, and may even prove fatal. The disease may occur as a result of both allergic and nonallergic mechanisms.

While there are several treatments available for relieving the symptoms and discomfort associated with asthma, there are no cures. Moreover, the current treatments often cause side effects that exacerbate the discomfort and precipitate other debilitating conditions. Mild asthma generally is treated with beta-adrenergic drugs, as well as antihistamines, especially in the case of children, to prevent or abort sporadic episodes. Moderately severe and severe asthma are generally treated with adrenergic agents and bronchodilators, as well as corticosteroids. Other actions caused by antiasthmatic agents which limit their widespread use include headache, fatigue, dry mouth, nervousness, and in some cases addiction and substance abuse. Recent advances in the understanding of the pathogenesis and treatment of asthma is discussed more fully in Am J Respir Crit. Care Med. 2008 May 15; 177(10):1068-73.

Because asthma is so prevalent in both children and adults, there is an ongoing need for agents that can treat the disease, or at least relieve the symptoms that accompany the disease, without causing undesirable side effects. Likewise, there is an ongoing need for compositions and methods for treating COPD. The present invention provides compositions and methods for the treatment of COPD and asthma and other advantages as described in the detailed description.

BRIEF SUMMARY OF THE INVENTION

One aspect of the present invention provides a method for treating chronic obstructive pulmonary disease comprising administering to a COPD patient a therapeutically effective amount of type V collagen, or a tolerogenic fragment thereof. In one embodiment of the methods described herein, the COPD patient has emphysema and/or chronic obstructive bronchitis. In another embodiment of the invention, the type V collagen or tolerogenic fragment thereof is administered orally, and may be administered at a dose of between 0.1 mg and 0.5 mg. In a further embodiment, the type V collagen or tolerogenic fragment thereof is administered intravenously, by intrapulmonary instillation, by inhalation, or intramuscularly. In certain embodiments, a combination of different routes may also be used. In yet another embodiment of the invention, the methods may further comprise administering to the COPD patient a bronchodilator, a corticosteroid of other known treatment for COPD.

Another aspect of the invention provides a method for treating asthma comprising administering to an asthma patient a therapeutically effective amount of type V collagen, or a tolerogenic fragment thereof. In one embodiment of the methods, the type V collagen or tolerogenic fragment thereof is administered orally, and may be administered at a dose of between 0.1 mg and 0.5 mg. In further embodiments, the type V collagen or tolerogenic fragment thereof is administered intravenously, by intrapulmonary instillation, by inhalation, or intramuscularly. In a yet further embodiment, the method further comprises administering to the asthma patient a corticosteroid, a bronchodilator and/or a leukotriene modifier, or other known treatment for asthma.

Another aspect of the invention provides a method for preventing the development of chronic obstructive pulmonary disease in a subject at risk for developing chronic obstructive pulmonary disease comprising administering to the subject a therapeutically effective amount of type V collagen, or a tolerogenic fragment thereof. In one embodiment, the type V collagen or tolerogenic fragment thereof is administered orally and may be administered at a dose of between 0.1 mg and 0.5 mg. In further embodiments, the type V collagen or tolerogenic fragment thereof is administered intravenously, by intrapulmonary instillation, by inhalation, or intramuscularly and may be administered by a combination of these routes.

A further aspect of the invention provides a method for preventing the development or worsening of asthma in a subject at risk for developing asthma comprising administering to the subject a therapeutically effective amount of type V collagen, or a tolerogenic fragment thereof. In one embodiment, the type V collagen or tolerogenic fragment thereof is administered orally and in certain embodiments, may be administered at a dose of between 0.1 mg and 0.5 mg. In a further embodiment, the type V collagen or tolerogenic fragment thereof is administered intravenously, by intrapulmonary instillation, by inhalation, intramuscularly, or by a combination of one or more of these routes.

One aspect of the present invention provides a method for identifying a COPD or asthma patient as a candidate for collagen V tolerance therapy comprising, contacting at least a portion of a sample of blood from the patient with collagen V or an antigenic fragment thereof; and measuring the level of antibodies that bind to the collagen V or antigenic fragment thereof (i.e., measuring the level of Type V collagen-specific antibodies); wherein the presence of antibodies bound to the collagen V is indicative of COPD or asthma. In this regard, collagen V-specific antibody level may be used in conjunction with other clinical factors as described herein in diagnosing COPD or asthma. In one embodiment, the collagen V or antigenic fragment thereof is conjugated to a bead. In a further embodiment, the measuring comprises contacting the antibodies that bind to the collagen V or antigenic fragment thereof with a fluorescently labeled anti-IgG antibody; and detecting by flow cytometry the amount of fluorescently labeled anti-IgG antibody bound to the antibodies bound to the collagen V.

Another aspect of the present invention provides a method for identifying an individual at risk for developing COPD or asthma, comprising: contacting at least a portion of a sample of blood from the individual with collagen V or an antigenic fragment thereof; and measuring the level of antibodies that bind to the collagen V or an antigenic fragment thereof (i.e., measuring the level of Type V collagen-specific antibodies); wherein the presence of antibodies that bind to the collagen V is associated with a higher risk than would be expected in an individual with no antibodies that bind to the collagen V. In one embodiment, the collagen V or antigenic fragment thereof is conjugated to a bead. In another embodiment, the measuring comprises contacting the antibodies that bind to the collagen V or antigenic fragment thereof with a fluorescently labeled anti-IgG antibody; and detecting by flow cytometry the amount of fluorescently labeled anti-IgG antibody bound to the antibodies bound to the collagen V.

In certain embodiments of the methods for diagnosing or measuring risk for developing COPD or asthma, the anti-IgG antibody used in the methods detects all IgG subtypes. In further embodiments, the anti-IgG antibody specifically detects the IgG1 subtype, or the IgG2 subtype, or the IgG3 subtype, or the IgG4 subtype. In this regard, a switch from one subtype to another subtype may occur during the course of disease and may indicate worsening of disease. Therefore, an increase in one subtype over time may indicate worsening of disease.

A further aspect of the invention provides a method for monitoring the progression of COPD or asthma in an individual comprising, contacting at least a portion of a first sample of blood from the individual with collagen V or an antigenic fragment thereof; measuring the level of antibodies that bind to the collagen V or antigenic fragment thereof in the first sample of blood; contacting at least a portion of a second sample of blood from the individual taken at a later time point, with collagen V or an antigenic fragment thereof; measuring the level of antibodies that bind to the collagen V or antigenic fragment thereof in the second sample of blood; and comparing the level of antibodies that bind to the collagen V or antigenic fragment thereof in the second sample of blood to the level of antibodies that bind to the collagen V or antigenic fragment thereof in the first sample of blood; wherein an increase in the level of antibodies bound to the collagen V in the second sample as compared to the first sample is indicative of worsening of COPD or asthma and a decrease in the level of antibodies bound to the collagen V in the second sample as compared to the first sample is indicative of amelioration of COPD or asthma. Other clinical indicators of COPD and asthma may be used in conjunction with the methods provided herein. In certain embodiments, an increase in anti-collagen V antibodies of a particular IgG subtype (e.g., IgG1, IgG2, IgG3, or IgG4) is indicative of a progression of COPD or asthma. In certain embodiments, the collagen V or antigenic fragment thereof is conjugated to a bead. In another embodiment, the measuring comprises contacting the antibodies that bind to the collagen V or antigenic fragment thereof with a fluorescently labeled anti-IgG antibody; and detecting by flow cytometry the amount of fluorescently labeled anti-IgG antibody bound to the antibodies bound to the collagen V. In certain embodiments of the methods for monitoring progression the anti-IgG antibody detects all IgG subtypes. In other embodiments, the anti-IgG antibody specifically detects the IgG1, IgG2, IgG3 or IgG4 subtype.

These and other aspects of the invention will be evident upon reference to the following detailed description and attached drawings.

DETAILED DESCRIPTION OF THE INVENTION

Type V Collagen

Collagen protein is made of polypeptide chains composed of a repeated sequence of amino acids primarily consisting of hydroxyproline (Hyp), glycine (Gly), and proline (Pro). Collagen is one of the most predominant proteins found in the human body, comprising about 80-85% of the extracellular matrix (ECM) in the dermal layer of normal (non-wounded) skin tissue.

Collagens are classified into several types based on sequence identity and function. Types I, II, & III collagen molecules make up the main fibers of most animal extracellular structures. Type I forms about 90% of the body's collagen and is the primary component of bone, skin and tendons. Type II makes up the major fibers of cartilage. Collagen fibers are arranged in rigid plates in bones, in parallel bundles in tendons, and in a dense meshwork in cartilage. Type I and lesser amounts of type III make up tendons and skin. Type IV collagen molecules make up very fine, unstriated fibers present in basal laminae. Type V Collagen (colV) is a minor collagen present in the lung (Madri and Furthmayr, Human Pathology, 11:353-366, 1980) and is located in the peribronchiolar connective tissues (Madri and Furthmayr, Am. J. Pathol., 94:323-332, 1979), alveolar interstitium (Konomi et al., 1984), and capillary basement membranes (Madri and Furthmayr, 1979, Supra). Over a dozen other collagen types are known but are less well characterized.

Collagen polypeptide chains are characterized by a core helical domain made up of repeating glycine-X-Y triplets and globular N-terminal and C-terminal domains. Three such chains are wound around one another in a superhelix to generate an individual ropelike collagen molecule.

Figure 3:
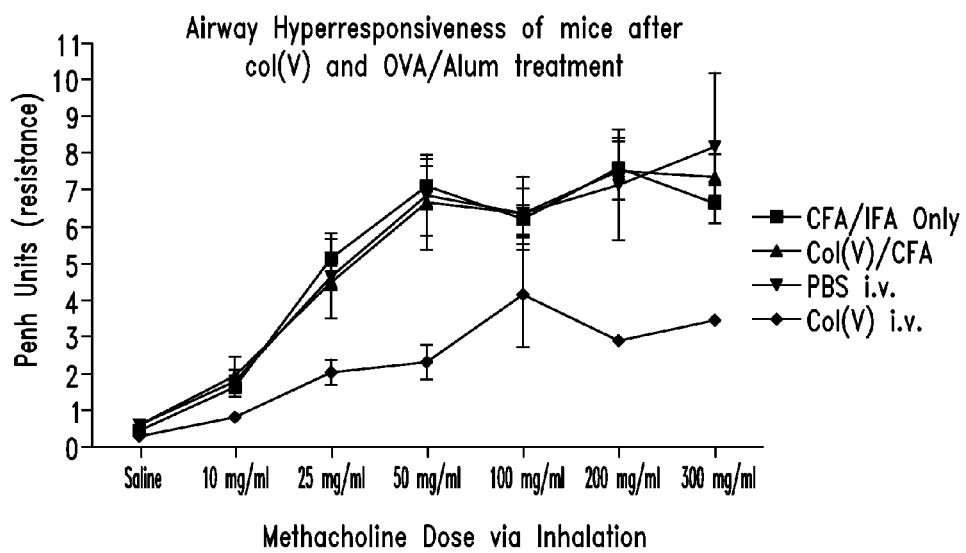
FIG. 3 shows prevention of ovalbumin-induced airway hyper-responsiveness in mice following intravenous administration of collagen V. n=5 in all groups except col V where n=2-5 for each data point.
Figure 4A:
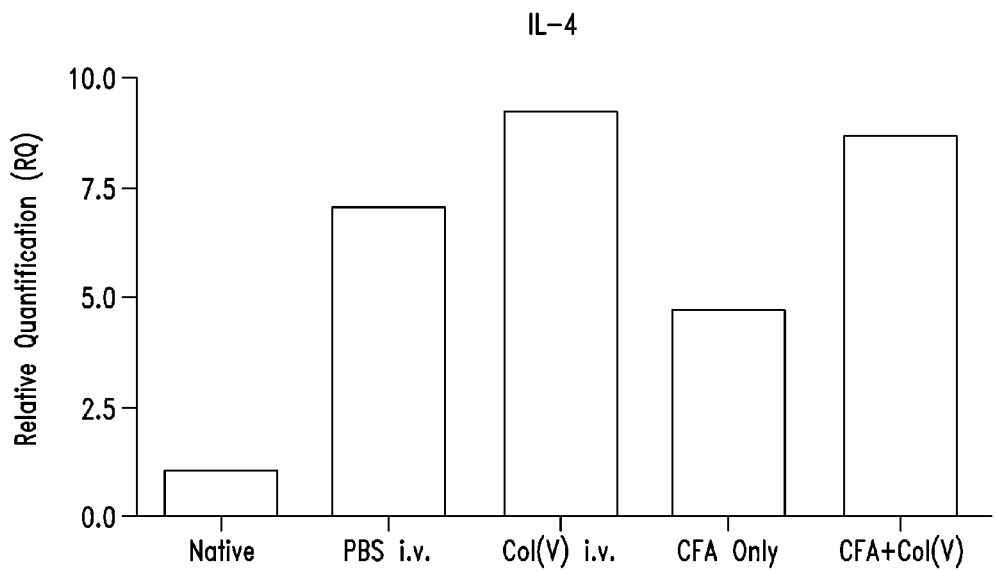
FIGS. 4A-4E are bar graphs showing induction of IFN-γ transcripts in lung mononuclear cells by intravenous administration of col(v). Quantitative PCR was performed for the IL-4, IL-5, IL-13, IFN-γ and IL-10 cytokines shown. Only Col(V) IV induced IFN-γ transcripts in lung mononuclear cells. Data represent lung mononuclear cells of RNA pooled from 5 mice in each group.
Figure 4B:
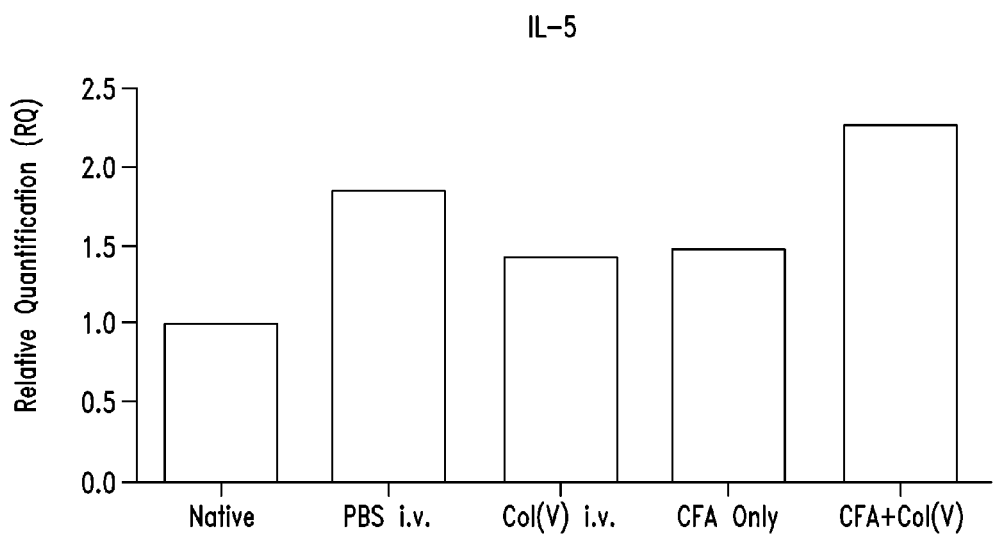
Figure 4C:
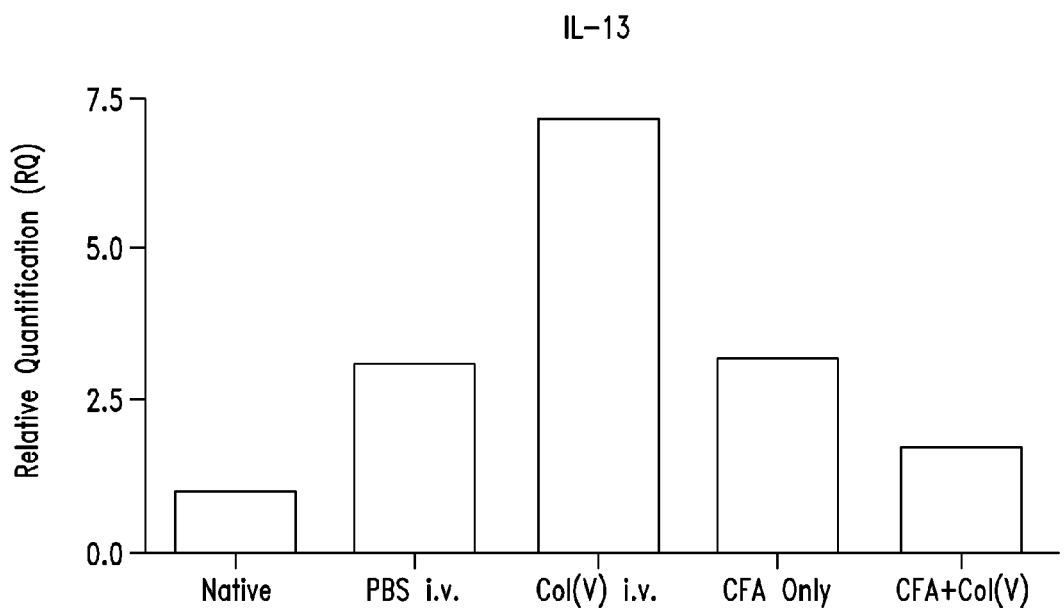
Figure 4D:
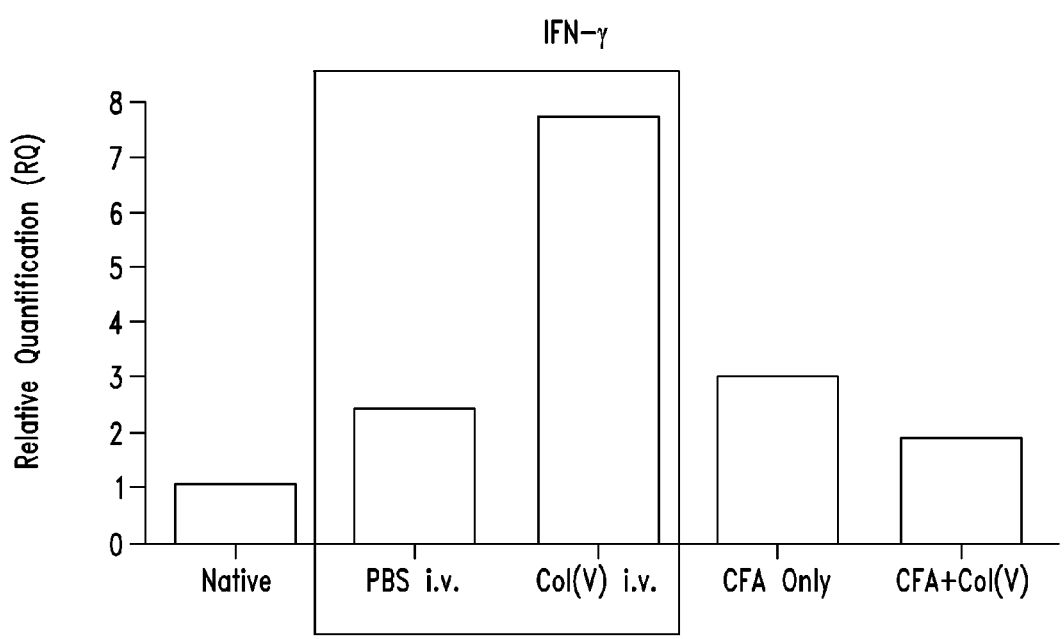
Figure 4E:
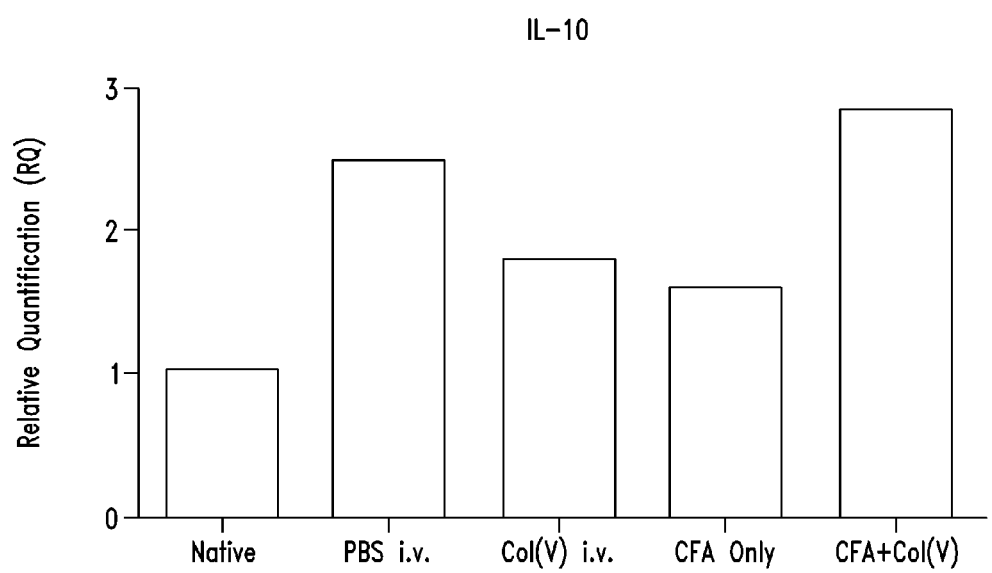

Previous work has demonstrated that autoimmunity to colV is associated with chronic allograft dysfunction (including obliterative bronchiolitis, bronchiolitis obliterans syndrome (BOS)), lung allograft rejection and with risk of developing IPF (see e.g., U.S. Pat. No. 7,348,005 and WO 2007/120947). Furthermore, this work showed that administration of colV induced tolerance to alloantigens and to colV (see e.g., WO 2007/120947; FIG. 10). However, prior to the present invention, no association with autoimmunity to colV had been shown in either asthma or COPD. In fact, previous findings had shown that patients with COPD do not have anti-col(V) DTH responses which were significantly different from that seen in normal subjects with no known lung disease (see WO 2007/120947, Example 2; FIG. 3). Therefore, the present invention is surprising in that, despite a previous observation that patients with COPD do not have elevated anti-colV DTH responses as compared to normal controls, it has now been found that COPD patients have elevated anti-colV antibodies (see e.g., Example 1, FIG. 1).

Thus, the present invention relates to inducing tolerance to colV in COPD and asthma patients, or in subjects at risk for developing these diseases.

ColV polynucleotide and polypeptide sequences are known to the skilled person and are available in public databases. Illustrative colV polynucleotides and polypeptides of the present invention include, but are not limited to Homo sapien collagen, type V, alpha 1 (COL5A1), mRNA NCBI Reference Sequence: NM_000093.3 version GI:89276750 (SEQ ID NO:1); alpha 1 type V collagen preproprotein [Homo sapiens]: Accession NP_000084, version GI:89276751 (SEQ ID NO:2); Homo sapien collagen, type V, alpha 2 (COL5A2), mRNA; accession NM_000393, version GI:89363016 (SEQ ID NO:3); alpha 2 type V collagen preproprotein [Homo sapiens]; accession NP_000384, version GI:89363017 (SEQ ID NO:4); Homo sapien collagen, type V, alpha 3 (COL5A3), mRNA; accession NM_015719, NM_015719.3, GI:110735434 (SEQ ID NO:5); collagen, type V, alpha 3 preproprotein [Homo sapien]; accession NP_056534, version NP_056534.2, GI:110735435 (SEQ ID NO:6).

As would be recognized by the skilled person, the preprocollagen is processed in a cell into procollagen which is exported from the cell and eventually formed into collagen fibrils and fibers. Thus, the present invention specifically contemplates procollagen and other processed or mature forms of collagen proteins described herein. In this regard, for example, amino acids 1-26 of SEQ ID NO:4 corresponds to the signal peptide which is cleaved during processing, amino acids 27-1229 is the collagen alpha-2(V) chain, and amino acids 1230-1499 correspond to the c-terminal propeptide. These positions within the sequences specifically disclosed herein would be recognized by the skilled person and are available through various public databases where annotation of sequences is provided. It should also be noted that certain amino acids of the collagen proteins are modified during processing (e.g., proline to hydroxyproline). Mature, modified forms of the type V collagen chains, particularly alpha-2 chains, are specifically contemplated herein. As noted elsewhere, the type V collagen and alpha chains thereof for use in the present invention may be purified from a variety of sources or produced recombinantly.

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising tolerogenic fragments.

The present invention, in another aspect, provides polypeptide fragments comprising at least about 5, 10, 15, 20, 25, 50, or 100 contiguous amino acids, or more, including all intermediate lengths, of a collagen polypeptide compositions set forth herein, such as those set forth in SEQ ID NOs: 2, 4 or 6, or those encoded by a polynucleotide sequence set forth in a sequence of SEQ ID NOs: 1, 3 or 5.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one embodiment, the polypeptide fragments and variants provided by the present invention are immunologically tolerogenic as described herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their tolerogenic activity as described herein and/or using any of a number of techniques well known in the art.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics, e.g., with tolerogenic characteristics. When it is desired to alter the amino acid sequence of a polypeptide to create an equivalent, or even an improved, tolerogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their tolerogenic utility or activity.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |

TABLE 1-continued

| Amino Acids | | | Codons |
|---|---|---|---|
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2);

glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the tolerogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., (1978) *A model of evolutionary change in proteins—Matrices for detecting distant relationships*. In Dayhoff, M. O. (ed.) *Atlas of Protein Sequence and Structure*, National Biomedical Research Foundation, Washington D.C. Vol. 5, Suppl. 3, pp. 345-358; Hein J. (1990) *Unified Approach to Alignment and Phylogenes*, pp. 626-645 *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Saitou, N. Nei, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a His tag for purification, or a targeting peptide. A fusion partner may, for example, assist in expressing the protein (an expression enhancer) at higher yields than the native recombinant protein. Other fusion partners may be selected so as to increase the solubility of the polypeptide or to enable the polypeptide to be targeted to desired intracellular compartments. Still further fusion partners include affinity tags, which facilitate purification of the polypeptide. In certain embodiments, a fusion partner increases the tolerogenicity of the polypeptide or increases its uptake by cells. In further embodiments, a fusion partner comprises an immune response enhancer.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

One embodiment of the invention involves fusion polypeptides, and the polynucleotides encoding them, wherein the fusion partner comprises a targeting signal capable of directing a polypeptide to the endosomal/lysosomal compartment, as described in U.S. Pat. No. 5,633,234. A tolerogenic polypeptide of the invention, when fused with this targeting signal, will associate more efficiently with MHC class II molecules and thereby provide enhanced in vivo stimulation of appropriate CD4$^+$ T cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

ColV protein may be purified from a variety of sources or may be purchased from a commercial source (Collaborative Biomedical Products/Becton, Dickinson and Company, Franklin Lakes, N.J. USA). In order to practice some embodiments it may be necessary to obtain pure or partially pure collagen or a tolerogenic fragment, epitope or antigenic portion thereof. These materials for example type V collagen or fragments thereof can be readily obtained by a variety of means including but not limited to animal sources, human cadavers, or recombinant means. Additional methods include partial digests of collagen such as type V collagen. In this regard, Human type V collagen may be extracted from human placenta or other sources and purified by differential NaCl precipitation (Seyer and Kang, 1989). For example, placental tissues are minced, washed, and suspended in 0.5 M acetic acid containing 0.2 M NaCl, and digested by pepsin at 4° C. Supernatants are aspirated from centrifuged specimens, the pellet collected and the extraction procedure repeated. The supernatants are combined from the two digests, and col(V) was purified from the supernatants by differential NaCl precipitation from 0.5 M acetic acid (Smith et al., 1985; Seyer and Kang, 1989). The type V collagen is generally soluble in 0.7 M NaCl and precipitated in 1.2 M NaCl.

For those embodiments where it is required to purify α(V) chains, the cycle of solubilization in acetic acid and NaCl precipitation may be repeated until a type V preparation with an α-chain ratio α1(V)/α2(V) of approximately 2 is obtained as determined by SDS-polyacrylamide gel electrophoresis (Smith et al., 1985), or other appropriate method known to the skilled artisan. Separation of α1(V) from α2(V) may be achieved by chromatography on DEAE-cellulose (Seyer and Kang, 1989) or other methods known to the skilled person, such as those described in Protein Purification Protocols, Ed. Shawn Doonan, Humana Press, 1996). The α1(V) and α2(V) chains may be eluted from the column, and purity confirmed by SDS-polyacrylamide gel electrophoresis as previously reported (Smith, Jr. et al, 1985). Intact col(V), or α1(V) and α2(V) chains may be diluted in PBS (0.5 mg/ml) or other appropriate buffer until use.

The present invention, in certain embodiments, provides polynucleotides encoding the collagen proteins of the present invention. Illustrative polynucleotides are those set forth in SEQ ID NOs:1, 3 and 5, and fragments thereof that encode a tolerogenic fragment of a collagen protein as described herein.

The terms "DNA" and "polynucleotide" are used essentially interchangeably herein to refer to a DNA molecule that has been isolated free of total genomic DNA of a particular species. "Isolated", as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989; Ausubel et al. (2001 *Current Protocols in Molecular Biology*, Greene Publ. Assoc. Inc. & John Wiley & Sons, Inc., NY, N.Y.) and other like references).

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably a tolerogenic variant or derivative, of such a sequence.

In other related embodiments, the present invention provides polynucleotide variants having substantial identity to the sequences disclosed herein in SEQ ID NOs: 1, 3 and 5, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the tolerogenic activity of the polypeptide encoded by the variant polynucleotide is not substantially diminished relative to a polypeptide encoded by a polynucleotide sequence specifically set forth herein. The term "variants" should also be understood to encompasses homologous genes of xenogenic origin.

In additional embodiments, the present invention provides polynucleotide fragments comprising or consisting of various lengths of contiguous stretches of sequence identical to or complementary to one or more of the sequences disclosed herein. For example, polynucleotides are provided by this invention that comprise or consist of at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In one embodiment, such polynucleotide variants encode polypeptides that have a level of tolerogenic activity of at least about 50%, preferably at least about 70%, and more preferably at least about 90%, 95%, 96%, 97%, 98%, 99%, or more, of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Saitou, N. Nei, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of tolerogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the tolerogenicity of a polypeptide. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced tolerogenic activity.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel et al. (2001-2008 *Current Protocols in Molecular Biology*, Greene Publ. Assoc. Inc. & John Wiley & Sons, Inc., NY, N.Y.).

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as pBLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke, G. and S. M. Schuster (1989) *J. Biol. Chem.* 264: 5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263-281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Tolerance

Immunological tolerance is defined as immune unresponsiveness to an antigen, usually an antigen implicated in causing disease. Although tolerance may be induced by administering antigens by different routes, oral tolerance refers to the oral administration of the antigen, which has resulted in suppression of disease activity in several animal models including experimental autoimmune encephalomyelitis-a rodent model of multiple sclerosis, myasthenia gravis, uveitis, insulin dependent diabetes, and collagen-induced arthritis (Faria and Weiner 1999). Early results from clinical trials in humans suggest that oral tolerance is effective in autoimmune uveitis, diabetes, nickel allergy, and possibly multiple sclerosis (Faria and Weiner 1999; Duda et al. 2000). There are few studies reporting oral tolerance induction in organ transplantation (Sayegh et al. 1996; Hancock et al. 1993; Ishido et al. 1999; Sayegh et al. 1992a; Sayegh et al. 1992b). In each report, tolerance was induced by feeding donor MHC-derived peptides or feeding allogeneic cells prior to transplantation (Sayegh et al. 1996; Hancock et al. 1993; Ishido et al. 1999; Sayegh et al. 1992a; Sayegh et al. 1992b). These techniques were effective in preventing rejection of cardiac and corneal allografts (Sayegh et al. 1996; Hancock et al. 1993; Ishido et al. 1999; Sayegh et al. 1992a; Sayegh et al. 1992b; Faria and Weiner 1999). In addition to diminished disease activity, immune suppression induced by oral tolerance in these studies was also quantitated by down regulation of delayed type hypersensitivity (DTH) responses to target antigens, as well as diminished cellular and humoral immunity (Faria and Weiner 1999; Mayer 2000; Garside and Mowat 1997).

There are three mechanisms by which oral (and other routes of administration) tolerance down regulates antigen-specific immune responses: 1. active suppression of antigen specific cells, 2. clonal anergy of antigen specific cells, and 3. clonal deletion of antigen specific cells (Faria and Weiner 1999, Miller et al. 1991; Chen et al. 1994; Chen et al. 1995). Although all three mechanisms can be operative simultaneously in response to oral tolerance, active suppression and clonal anergy are the key mechanisms of immune suppression induced by oral tolerance (Faria and Weiner 1999).

Active suppression describes the regulation of one lymphocyte subset by another in an antigen-specific manner. Depending on the antigen and disease state, the suppressor cells may be CD4+ and/or CD8+ T-lymphocytes which migrate from peripheral lymphoid tissues, such as spleen and peripheral lymph nodes, to sites of disease activity. Adoptive transfer of these cells to naive recipients has confirmed the role of these cells in active suppression in rodent models of ovalbumin-induced hypersensitivity, and multiple sclerosis. In vitro evidence of active suppression is demonstrated by data showing that tolerized lymphocytes from animals can suppress proliferation of other antigen-specific T-lymphocytes across a transwell cell culture system (Faria and Weiner 1999; Miller et al. 1991).

Clonal anergy refers to unresponsiveness of antigen-specific T-lymphocytes, which is characterized by diminished proliferation after exposure to an antigen, and is involved in oral tolerance in several animal models. Anergy could be the result of production of soluble suppressive factors by CD4+ or CD8+ T-lymphocytes themselves, other T-lymphocytes or cells in the local environment, or as result of decreased expression of appropriate costimulatory molecules (Faria and Weiner 1999). Clonal deletion refers to the elimination of antigen-specific T-lymphocytes, but has been reported rarely as a mechanism of oral tolerance to an antigen (Chen et al. 1995).

The soluble mediators that suppress the immune response during oral tolerance are derived mainly from regulatory or suppressor T-lymphocytes (Faria and Weiner 1999). There are five types of T-lymphocytes described by the cytokines they produce: Th1-type that produce interleukin-2 (IL-2) and gamma interferon ($\gamma$IFN); Th2-type that produce IL-4 and IL-10; Th3-type that produce high levels or transforming growth factor beta (TGF-$\beta$), alone, or in conjunction with very low levels of IL-4, IL-10, or $\gamma$IFN; Tr1 cells that produce high levels of IL-10 in conjunction with low levels of TGF-$\beta$ (Faria and Weiner et al. 1999; Mayer 2000; Garside and Mowat 1997; Groux et al. 1997); and Th17 cells that produce IL-17 (see e.g., Immunol Rev. 2008, 226:87-102; Nature.

2006 May 11; 441(7090):235-8). Since Th3, Th2, and Tr1-T-lymphocytes have been shown to be the major mediators of active suppression induced by oral tolerance, then TGF-β, IL-4 and IL-10 are believed to be key cytokines in this process (Teng et al. 1998; Shi et al. 1999b). A report from Barone et al., and others showing that oral tolerance induction occurred in the absence of these cytokines suggests that other mediators or cells could suppress the immune response (Barone et al. 1998; Shi et al. 1999a).

Although studies of oral tolerance have focused on T-lymphocyte-derived cytokines that suppress immune responses, nitric oxide, which is not produced by T-lymphocytes, is known to be a potent suppressor of alloimmmune responses (Garside and Mowat 1997). These data and others showing that nitric oxide modulates apoptosis, which is involved in the rejection response (Meyer et al. 1998; Kallio et al. 1997; Shiraishi et al. 1997; Shiraishi et al. 1995; Medot-Pirenne et al. 1999), suggests that nitric oxide could be a mediator of oral tolerance and prevent the rejection response. TGF-β, is a potent inducer of nitric oxide synthesis, and is a key mediator of active suppression in oral tolerance (Faria and Weiner 1999; Meyer et al. 1998; Vodovotz et al. 1998; Vodovitz et al. 1999). Therefore, immunosuppression induced by TGF-β in the tolerized host could be mediated, in part, by nitric oxide. However, production of nitric oxide in response to oral tolerance is unknown.

Antigen-specific T-lymphocyte activation induced by APCs requires bi-directional interaction between the T-lymphocyte and APC. Initially, APCs present MHC molecules that bind to the T-cell-receptor which stimulates upregulated expression of CD40-ligand (CD40L) on T-lymphocytes. CD40L, in turn, binds to its receptor, CD40, on the APC. Signaling through CD40 induces the expression of CD80 and CD86 on the APC which, upon binding to their receptor, CD28, on the T-lymphocyte, results in co-stimulation and subsequent T-lymphocyte activation (Liu et al. 1999; Li et al. 1999; Lederman and Siciu-Foca 1999). Although studies of oral tolerance induction have focused on T-lymphocyte function, a recent study from Taams et al (1998), reported that tolerance induction may affect function of APCs, with similar data from other investigators (Wu et al. 1998; Finkelman et al. 1996; Viney et al. 1998). For example, a report from Wu. et al (1998), showing that expression of CD80 is decreased on APCs from the lymph nodes and spleens of orally tolerized mice suggests that ineffective APCs could contribute to impaired T-lymphocyte activation in tolerized recipients. Furthermore, studies in vitro showing that suppressor T-lymphocytes inhibit expression of CD86 in APCs highlights another mechanism of how tolerance induces impaired APC function (Liu et al. 1999; Li et al. 1999; Lederman and Siciu-Foca 1999).

Administration of col(V) prevents proliferative responses to alloantigens, in addition to preventing proliferative responses to itself, and prevents the development of acute rejection pathology in recipient lungs (see e.g., U.S. Pat. No. 7,348,005; WO 2007/120947). Thus, col(V) may induce anergy to donor alloantigens and to itself; or alternatively, the lack of proliferative responses to donor antigens and to colV may be due to clonal deletion of alloantigen-specific lung lymphocytes; or yet alternatively may result from suppressor cell activity.

Without being bound by theory, tolerance induction by colV may be induced through linked suppression (see, e.g., Hum Immunol. 2008 November; 69(11):715-20). Also, it is thought that differential binding of colV to the collagen receptors on lymphocytes, leading to differential activation signals may be involved (see e.g., Cell Signal. 2006 August; 18(8):1108-16). For example, only collagen V induced IL-17 signaling in T cells.

Oral administration of antigens is an effective method of inducing peripheral T-cell tolerance. This phenomenon, often referred to as oral tolerance, has been well studied in various models of autoimmune diseases in animals including encephalomyelitis, uveitis, diabetes, myasthenia gravis, and arthritis. However, the mechanisms for inducing tolerance are not completely understood. All of the known mechanisms for tolerance induction, including clonal anergy, clonal deletion, and regulation by IL-4, IL-10, or TGF-beta-mediated active suppression may have a role in oral tolerance (Faria and Weiner, 1999). Generally, higher doses of antigen are reported to induce anergy or clonal deletion (Chen et al., 1995; Whitacre et al., 1991), whereas low doses induce cytokine regulation and active suppression (Faria and Weiner, 1999; Chen et al., 1994). In the animal model of cardiac transplantation, oral administration of allogeneic splenocytes has been shown to be effective in tolerance induction by bypassing Th1 activation and selectively stimulating induction of Th-2 derived inhibitory cytokines such as IL-4 (Hancock et al., 1993; Ishido et al., 1999).

Thus, oral tolerance is a method of downregulating an immune response in a subject by orally administering an antigen (i.e. by feeding) to the subject. Oral tolerance is characterized by decreased levels of systemic antibody production, as well as decreased delayed type hypersensitivity responses (DTH), T cell proliferation, cytotoxic responses and graft rejection (Alpan et al. 2001. J. Immunol. 166:4843-52; Chen et al. 1995. Nature 376:177-80; Weiner. 1997. Imm. Today. 7:335-44; Sayegh et al. 1992. Transplantation. 53:163-6).

Other routes for inducing tolerance are also contemplated herein, in particular by intramuscular, subcutaneous, intradermal and intravenous injection. Intradermal injections are contemplated herein where low doses tend to induce tolerance and high doses induce an immune response.

Studies of tolerance have focused primarily on the effect of the tolerizing antigen on T-lymphocyte function, and the role of T-lymphocytes in suppressing immune activation (Faria and Weiner 1999; Mayer 2000; Garside and Mowat 1997). However, immune responses to any antigen require interactions between APCs and T-lymphocytes, and the T-lymphocyte may affect APC function (Liu et al. 1999; Li et al. 1999; Lederman and Siciu-Foca 1999). Therefore, down-regulated antigen presentation by APCs from tolerized hosts could contribute to tolerance induction either indirectly as a result of interactions with suppressor T-lymphocytes, or possibly as a result of direct effects of the tolerizing antigen on the APC.

Thus, in certain aspects of the invention, the present invention provides methods for restoring or reinforcing self-tolerance to colV in COPD and asthma patients. One embodiment is a method of treating COPD or asthma by administering colV either by oral therapy (Yasufuku et al, 2001; Yasufuku, et al, 2002) interstitially into the lung or by other desensitization strategies on a dosage regimen designed to increase the patient tolerance for collagens including, but not necessarily limited to colV and antigenic components and variants thereof.

By "tolerogenic fragment" is meant a fragment that can induce tolerance to the full-length protein of which it is a fragment (e.g., full-length type V collagen, and tolerogenic fragments thereof). In certain embodiments, a tolerogenic fragment can induce tolerance to the full-length type V collagen at least as well as the full-length type V collagen protein can and in certain embodiments may be more effective than the full-length collagen protein at inducing tolerance. However, in certain embodiments, a tolerogenic fragment induces tolerance to the full-length type V collagen but may not induce tolerance as effectively as the full-length type V collagen protein. Such tolerogenic fragments may still be useful in the present invention particularly where said tolerogenic fragments have other advantageous properties, such as ease of preparation or purification as compared to the full-length protein. As would be recognized by the skilled person, a variety of known assays can be used to assess induction of tolerance, including measuring delayed-type hypersensitivity (DTH) responses, measuring cytokine productions by ELISA or other methods, T cell proliferation or cytotoxicity assays, B cell proliferation assays, antibody production, and the like. Such assays are known in the art and are described, for example, in Current Protocols in Immunology, Edited by: John E. Coligan, Ada M. Kruisbeek, David H. Margulies, Ethan M. Shevach, Warren Strober (2001 John Wiley & Sons, NY, N.Y.); Ausubel et al. (2001 Current Protocols in Molecular Biology, Greene Publ. Assoc. Inc. & John Wiley & Sons, Inc., NY, N.Y.); U.S. Pat. No. 7,348,005; and elsewhere.

Thus, a tolerogenic fragment is a fragment of a tolerogenic polypeptide such as type V collagen, or any one or more of the alpha chains thereof, that itself is immunologically tolerogenic (i.e., induces tolerance) with regard to the specific B-cells and/or T-cells that recognize the polypeptide via their surface receptors (e.g., B cell antibody receptor or T cell receptor). Tolerogenic fragments may generally be identified using well known techniques, such as those summarized in Paul, Fundamental Immunology, 3rd ed., (Raven Press, 1993) and references cited therein. Such techniques include screening polypeptides for the ability to reduce T cell and/or B cell reactivity. As used herein, antisera and antibodies are "antigen-specific" if they specifically bind to an antigen (i.e., they react specifically with the protein in an ELISA or other immunoassay, and do not react detectably with unrelated proteins). Such antisera and antibodies may be prepared as described herein, and using well-known techniques.

In one embodiment, a tolerogenic fragment of a polypeptide of the present invention is a portion that induces B cell and/or T cell tolerance at a level that is not substantially less than the tolerogenic activity of the full-length polypeptide (e.g., in an appropriate assay such as antibody production, which may be measured by ELISA, and/or T cell reactivity assay (T cell proliferation or cytokine production assay). Preferably, the level of tolerogenic activity of the tolerogenic portion is at least about 50%, 55%, 60%, 65%, 70%, 75%, 80%, 85%, or greater than about 90%, 91%, 92%, 93%, 94%, 95%, 96%, 97%, 98%, or 99% of the tolerogenic activity of the full-length polypeptide. In some instances, tolerogenic fragments will be identified that have a level of tolerogenic activity greater than that of the corresponding full-length polypeptide, e.g., having greater than about 100%, 110%, 120%, 130%, 140% or 150% or more tolerogenic activity.

In certain embodiments, tolerogenic fragments may be identified using computer analysis, such as the Tsites program (see Rothbard and Taylor, EMBO J. 7:93-100, 1988; Deavin et al., Mol. Immunol. 33:145-155, 1996), which searches for peptide motifs that have the potential to elicit Th responses. CTL peptides with motifs appropriate for binding to murine and human class I or class II MHC may be identified according to BIMAS (Parker et al., J. Immunol. 152:163, 1994) and other HLA peptide binding prediction analyses. Alternatively, portions that bind to a particular MHC molecule can be identified by using defined peptide binding motifs such as those described in Rammensee et al., Immunogenetics 41:178-228, 1995. To confirm peptide binding to murine and human class I or class II MHC molecules, peptide binding assays known in the art may be used. To confirm immunogenicity or tolerogenicity, a peptide may be tested using an HLA A2 or other transgenic mouse model and/or an in vitro stimulation assay using dendritic cells, fibroblasts or peripheral blood cells.

It should be noted that in certain embodiments, a tolerogenic fragment of the invention is also an immunogenic fragment. In this regard, as would be recognized by the skilled artisan, highly immunogenic fragments, such as immunodominant epitopes of proteins like colV, may be tolerogenic when administered correctly, e.g., generally in low doses over extended periods of time. Thus, the present invention also contemplates the identification and use of immunogenic fragments of colV where such immunogenic fragments may be used to induce tolerance. In this regard, the level of immunogenic activity of an immunogenic portion is at least about 50%, 55%, 60%, 65%, 70%, 75%, 80%, 85%, or greater than about 90%, 91%, 92%, 93%, 94%, 95%, 96%, 97%, 98%, or 99% of the immunogenic activity of the full-length polypeptide. In some instances, immunogenic fragments will be identified that have a level of immunogenic activity greater than that of the corresponding full-length polypeptide, e.g., having greater than about 100%, 110%, 120%, 130%, 140% or 150% or more immunogenic activity.

The same analyses may be used to identify immunogenic fragments that are used to identify tolerogenic fragments, including using computer analysis, such as the Tsites program (see Rothbard and Taylor, EMBO J. 7:93-100, 1988; Deavin et al., Mol. Immunol. 33:145-155, 1996), which searches for peptide motifs that have the potential to elicit Th responses. CTL peptides with motifs appropriate for binding to murine and human class I or class II MHC may be identified according to BIMAS (Parker et al., J. Immunol. 152:163, 1994) and other HLA peptide binding prediction analyses. Alternatively, portions that bind to a particular MHC molecule can be identified by using defined peptide binding motifs such as those described in Rammensee et al., Immunogenetics 41:178-228, 1995. To confirm peptide binding to murine and human class I or class II MHC molecules, peptide binding assays known in the art may be used. To confirm immunogenicity or tolerogenicity, a peptide may be tested using an HLA A2 or other transgenic mouse model and/or an in vitro stimulation assay using dendritic cells, fibroblasts or peripheral blood cells.

Intact type V collagen or any one or more of its component alpha chains that have tolerogenic or immunogenic activity, are contemplated for use in the methods of the present invention. As such, a tolerogenic fragment or immunogenic fragment of collagen V may refer to a fragment of intact type V collagen or may refer to a tolerogenic or immunogenic fragment of any one of the component alpha chains. In certain embodiments, the colV as used herein may comprise the collagen molecule composed of the three alpha chains. In a further embodiment, colV may comprise any one or more of the alpha chains, such as those set forth in SEQ ID NOs:2, 4 or 6, encoded by the polynucleotides set forth in SEQ ID NOs:1, 3, or 5, or a tolerogenic fragment or an immunogenic fragment thereof.

In certain embodiments, two or more tolerogenic or immunogenic fragments may be used concurrently, either administered separately, mixed in a composition, or as a fusion protein. In this regard, any number of tolerogenic fragments or immunogenic fragments may be used to induce tolerance to colV, such as 2, 3, 4, 5, 6, 7, 8, 9, 10 or more tolerogenic or immunogenic fragments, either in a composition as separate fragments or as a fusion protein, with or without linkers. In certain embodiments, 11, 12, 13, 14, 15, 16, 17, 18, 19, 20, 21, 22, 23, 24, 25, 26, 27, 28, 29, 30 or more fragments may be used in the methods of the present invention.

Detecting the presence of antibodies to collagen in accordance with some embodiments may be accomplished using any of a number of immunoassay procedures, such as by ELISA procedures. A wide range of immunoassay techniques is available as can be seen by reference to standard immunoassay textbooks these include, but are not limited to singlesite and two-site or "sandwich" assays of the non-competitive types, as well as the traditional competitive binding assays.

Sandwich assays are among the most useful and commonly used antibody based assay methods and may be used to practice various embodiments. A number of variations of the sandwich assay technique exist, and all are intended to be encompassed by various embodiments. Briefly, in a typical assay to detect antibodies in a sample, an unlabelled antigen is immobilized on a solid substrate and the sample to be tested is contacted with the bound antigen molecule. After a suitable period of incubation, i.e. for a period of time sufficient to allow formation of an antibody-antigen complex, a second antibody such as anti-human IgG, labeled with a reporter molecule capable of producing a detectable signal, is then added and incubated, allowing time sufficient for the formation of an antibody-antigen-labeled antibody. Any unreacted material is washed away, and the presence of the antibody to be detected in the sample is determined by observation of a signal produced by the reporter molecule. The results may either be qualitative, e.g., by simple observation of the visible signal, or may be quantitated by comparing the signal generated by a sample of interest with a control sample containing known amounts of antibody to be detected. Variations on this assay include a simultaneous assay, in which both the sample and labeled antibody are added simultaneously to the bound antigen. These techniques are well known, including any minor variations as will be readily apparent to those in the art. In the typical sandwich assay, antigen is immobilized, for example by being either covalently or passively bound to a solid surface. In some embodiments the solid surface is typically glass or a polymer, the most commonly used polymers being cellulose, polyacrylamide, nylon, polystyrene, polyvinyl chloride or polypropylene. The solid supports may be in the form of tubes, beads, discs, or microplates, or any other surface suitable for conducting an immunoassay. Various binding processes are well-known in the art and generally consist of crosslinking, covalent binding or physical adsorption of the antigen to a given surface. The immobilized antigen is then washed in preparation for the addition of the test sample. An aliquot of the sample to be tested is then contacted with the immobilized antigen and incubated for a period of time sufficient (e.g. 2-40 minutes) and under suitable conditions (e.g. 25° C.) to allow binding of any antibody to collagen present in the sample. The actual length of contact time, buffer conditions, temperatures and the like are readily adjustable parameters and are typically readily arrived at for a given test. Following the incubation period, the immobilized antigen including any bound antibody is washed and dried, and incubated with a second antibody specific for the bound antibody, for example anti-human IgG. The second antibody is linked to a reporter molecule which is used to indicate the binding of the second antibody to the antibody-immobilized antigen complex.

One particular method for measuring antibodies to colV is described in WO 2007/120947. Specifically, this bead assay detects antibodies to type V collagen as may be present in serum and/or lung lavage fluid from patients that have an autoimmune response type V collagen. Type V collagen-coated beads along with other necessary reagents are provided for this assay. Briefly, a typical assay is as follows: 1) Streptavidin-coated beads (e.g., such as those from Polyscience, Warrington, Pa.) are washed with sterile PBS. Beads are suspended in an appropriate volume of PBS with human type V collagen. 2) A positive control is generated by following the same procedures in 1 above, using rabbit antibody to human collagen V antibody (Bioten) (Abeam, Cambridge, Mass.). 3) For each assay, conjugated beads are washed in PBS, and incubated in PBS plus serum of lung lavage fluid. The beads are then washed with PBS containing 10% FCS. 4) The beads are then suspended in sterile PBS+10% FBS and incubated at room temperature with secondary antibody. Typically, anti-human IgG antibody conjugated with R-PE is used (Sigma, Saint Louis) although as would be understood by the skilled artisan, other suitable antibodies are available. In this regard, anti-human IgG1-, IgG2-, IgG3-, or IgG4-specific antibodies may be used in certain embodiments in order to detect switching from one subtype to another during the course of disease. The beads are washed in PBS containing 10% FCS, suspended in PBS/FCS solution and analyzed using a flow cytometer. For the positive control, known amounts of anti-colV antisera or antibody may be added to the bead assay.

Typically, antibodies to colV found in COPD and asthma patients are IgG but other classes of antibodies may also be present, such as IgM. Further, in certain embodiments of the present invention, the subtype of IgG antibodies to type V collagen as may be present in serum and/or lung lavage fluid from patients changes through the course of the disease. In this regard, the IgG subtype switching may occur during the course of a disease and certain subtypes may be indicative of worsening disease. Thus, any one or more of the IgG subtypes may be present during the course of disease, e.g. IgG1, IgG2, IgG3, or IgG4, or any combination thereof. The present invention provides for methods for detecting Type V collagen-specific IgG1, IgG2, IgG3, IgG4 subtype antibodies using the bead assay as described herein. As would be recognized by the skilled person, IgG subtype-specific antibodies are commercially available and may be used in the methods described herein. In certain embodiments, an increase in IgG1 indicates worsening of disease. In another embodiment, a switch to IgG2 subtype indicates worsening of disease. In further embodiment, a switch to IgG3 subtype indicates worsening of disease. In yet an additional embodiment, a switch to IgG4 subtype indicates worsening of disease.

Compositions, Pharmaceutical Compositions and Methods of Use

Administration of the tolerogenic compounds or compositions of the invention, or their pharmaceutically acceptable salts, in pure form or in an appropriate pharmaceutical composition, can be carried out via any of the accepted modes of administration of agents for serving similar utilities. As noted elsewhere herein, one route contemplated herein for inducing tolerance is oral administration. However, any of a variety of other routes may also be used, in particular including intravenous, intramuscular, intradermal, subcutaneous injection, and other routes. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other immunosuppressive agents) and/ or suitable excipients such as salts, buffers and stabilizers may, but need not, be present within the composition.

Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the onset of an anti-colV immune response or clinical indication of such a response is considered effective.

In certain embodiments, the amount administered is sufficient to result in reduced immune activity as described elsewhere herein (e.g., T cell response, B cell response, anti-colV antibody level, and the like). The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The compositions of the present invention may be administered alone or in combination with other known treatments, such as immunosuppressive regimens, radiation therapy, chemotherapy, transplantation, oral collagen therapy, immunotherapy, hormone therapy, photodynamic therapy, etc.

Typical routes of administering these and related pharmaceutical compositions thus include, without limitation, oral, topical, transdermal, inhalation, intrapulmonary instillation, parenteral, sublingual, buccal, rectal, vaginal, and intranasal. The term parenteral as used herein includes subcutaneous injections, intravenous, intramuscular, intrasternal injection or infusion techniques. Compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

In certain embodiments, the therapeutic compound(s) are directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Certain oral pharmaceutical compositions contain between about 4% and about 75% of the compound of the invention. Certain pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

In certain embodiments, the dose of colV administered orally is from 0.001 mg to 500 mg per day. In one particular embodiment, the oral dose of colV as described herein is from 0.01 mg to 50 mg per day. In a further embodiment, the oral dose of colV as described herein is from 0.1 mg to 0.5 mg per day. In one embodiment, the oral dose of colV is 0.01, 0.02, 0.03, 0.04, 0.05, 0.06, 0.07, 0.08, 0.09, or 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg per day. In another embodiment, the oral dose of colV may be 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0 mg per day. In certain embodiments, the dose may given in a single dose, or may be given in multiple doses over the course of the day, for example in 2, 3 or 4 doses per day for a total of a particular mg/day dose.

As described elsewhere herein, in certain embodiments, a therapeutically effective dose of colV as used herein is a dose sufficient to induce tolerance to colV measured using any of a variety of methods as described herein. In certain embodiments, induction of tolerance to colV results in a decrease in serum anti-colV antibodies as measured using the methods described herein, such as an ELISA. In a further embodiment, a therapeutically effective dose of colV as used herein is a dose sufficient to induce T cell tolerance to colV as measured using any of a variety of methods as described herein, such as cytokine release assays, intracellular cytokine staining and flow cytometry, ELISPOT, and the like. Functional T cell assays, such as proliferation of cytotoxicity assays may also be used.

Compounds of the invention, or pharmaceutically acceptable salts thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

The compounds of the present invention may be administered to an individual afflicted with a disease or disorder as described herein, such as COPD and severe and persistent asthma. For in vivo use for the treatment of human disease, the compounds described herein are generally incorporated into a pharmaceutical composition prior to administration. A pharmaceutical composition comprises one or more of the compounds described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compounds described herein may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

In certain embodiments, adjuvants which assist in inducing tolerance include dexamethasone (see e.g., Y. Kang, et al., J. Immunol. 2008, 180: 5172-5176), lipopolysaccharides (LPS) and cholera toxin β-subunit and may be added to the formulations. Certain other tolerogenic carriers are also contemplated for use with the colV compositions of the present invention. Such carriers include mineral oil carriers such as incomplete, Freund's adjuvant (IFA) or complete Freund's adjuvant (CFA). IFA is an emulsion of mineral oil. CFA is a preparation of mineral oil containing various amounts of killed organisms of *Mycobacterium*. However, IFA and CFA are not allowed for human use because the mineral oil is not metabolizable and cannot be degraded by the body.

In certain embodiments, fat emulsions, which have been in use for many years for intravenous nutrition of human patients, can also act as a vehicle for tolerogenic polypeptide therapy using the polypeptides of the present invention. Two examples of such emulsions are the available commercial fat emulsions known as Intralipid and Lipofundin. "Intralipid" is a registered trademark of Kabi Pharmacia, Sweden, for a fat emulsion for intravenous nutrition, described in U.S. Pat. No. 3,169,094. "Lipofundin" is a registered trademark of B. Braun Melsungen, Germany. Both contain soybean oil as fat (100 or 200 g in 1,000 ml distilled water: 10% or 20%, respectively). Egg-yolk phospholipids are used as emulsifiers in Intralipid (12 g/l distilled water) and egg-yolk lecithin in Lipofundin (12 g/l distilled water). Isotonicity results from the addition of glycerol (25 g/l) both in Intralipid and Lipofundin. It is believed that these vehicles are actually biologically active carriers which when complexed with the suspected auto-antigen, promote a TH1 to TH2 shift of the autoimmune T cells. In certain embodiments, such a vehicle is a fat emulsion comprising 10-20% triglycerides of plant and/or animal origin, 1.2-2.4% phospholipids of plant and/or animal origin, 2.25-4.5% osmo-regulator, 0-0.05% anti-oxidant, and sterile water to 100%.

In certain embodiments, colV or toleragenic fragments thereof may be linked to the diphtheria toxin receptor to enhance GI uptake.

The tolerogenic compositions of the present invention may be used to treat asthma and COPD and other pulmonary diseases associated with autoimmunity to colV. Thus, in one embodiment, the present invention provides a method for treating chronic obstructive pulmonary disease comprising administering to a COPD patient a therapeutically effective amount of type V collagen, or a tolerogenic fragment thereof, or an immunogenic fragment thereof administered in a dose effective to induce tolerance. In this regard, a COPD patient may have emphysema or chronic obstructive bronchitis.

Another aspect of the invention provides a method for treating asthma comprising administering to an asthma patient a therapeutically effective amount of type V collagen, or a tolerogenic fragment thereof, or an immunogenic fragment thereof administered in a dose effective to induce tolerance. In this regard, the asthma patient may have severe, persistent asthma. In another embodiment, the present invention provides methods for reducing the severity of asthma in an asthma patient.

The present invention further provides, a method for preventing the development of chronic obstructive pulmonary disease in a subject at risk for developing chronic obstructive pulmonary disease comprising administering to the subject a therapeutically effective amount of type V collagen, or a tolerogenic fragment thereof.

As noted elsewhere herein, intact colV or any one or more of its component α chains may be administered, or a tolerogenic fragment of any of the aforementioned molecules. Further, also as noted elsewhere herein, an immunogenic fragment of intact colV or any one or more of its component α chains may be administered in any of the methods described herein, using a dose effective to induce tolerance to colV. Such a dose will vary depending upon a variety of factors including the activity of the specific proteins or fragments employed; the metabolic stability and length of action of these compounds; the age, body weight, general health, sex, and diet of the patient; the mode and time of administration; the rate of excretion; the drug combination; the severity of the particular disorder or condition; and the subject undergoing therapy. Thus, such tolerogenic doses may be determined empirically using known testing protocols or by testing the compositions in model systems known in the art and extrapolating therefrom. Controlled clinical trials may also be performed. Dosages may also vary with the severity of the condition to be alleviated.

As would be readily appreciated by the skilled artisan, a variety of factors can be assessed to determine the effectiveness of the compounds and methods of the invention for treating, preventing, or reducing the severity of COPD or asthma. Such factors include typical clinical symptoms of asthma or COPD which can be assessed by the skilled clinician. These symptoms may include, but are not limited to: for asthma: wheezing; chest tightness or pain; rapid heart rate; sweating; peak flow rates as measured by a peak flow meter; frequent cough, especially at night; loss of breath easily or shortness of breath; feeling very tired or weak when exercising; wheezing or coughing after exercise; feeling tired, easily upset, grouchy, or moody; decreases or changes in lung function as measured on a peak flow meter; signs of a cold, or allergies (sneezing, runny nose, cough, nasal congestion, sore throat, and headache); trouble sleeping. Such factors include typical clinical symptoms of COPD such as, but not limited to the amount of sputum produced; thickness or stickiness of sputum; sputum color or the presence of blood in the sputum; severity of shortness of breath, cough and/or wheezing; ankle swelling; forgetfulness, confusion, slurring of speech and sleepiness; trouble sleeping; using more pillows or sleeping in a chair instead of a bed to avoid shortness of breath; an unexplained increase or decrease in weight; fatigue and lack of energy that is persistent; a lack of sexual drive; morning headaches, dizzy spells, restlessness.

The compositions and methods of the present invention can be used in conjunction with other known treatments for COPD and asthma, such as, but not limited to corticosteroids (e.g., prednisone, fluticasone, methylprednisolone), bronchodilators (e.g., short- and long-acting β2-agonists, theophylline, pirbuterol, ephedrine, albuterol, salmeterol, levalbuterol, clenbuterol ipratropium bromide), and leukotriene modifiers (e.g., montelukast, zafirlukast, zileuton).

REFERENCES

The following references, to the extent that they provide exemplary procedural or other details supplementary to those set forth herein, are specifically incorporated herein by reference. Chen, Inobe, Marks, Gonnella, Kuchroo, Weiner, "Peripheral deletion of antigen-reactive T cells in oral tolerance," Nature, 376:177-180, 1995. Chen, Kuchroo, Inobe, Hafler, Weiner, "Regulatory T-cell clones induced by oral tolerance: suppression of autoimmune encephalomyelitis," Science, 265:1237-1240, 1994. Chiang, Mainardi, Seyer, "Type V(A-B) collagen induces platelet aggregation," J. Lab. Clin. Med., 95:99-107, 1980. Cremer, Ye, Terato, Owens, Seyer, Kang, "Type XI collagen-induced arthritis in the Lewis rat: characterization of cellular and humoral immune responses to native types XI, V, and II collagen and constituent α-chains," J. Immunol. 153:824-832, 1994. Danzer, Kirchner, Rink, "Cytokine interactions in human mixed lymphocyte culture," Transplantation, 57(11):1638-1642, 1994. DeMeester, Rolfe, Kunkel, Swiderski, Lincoln, Deeb, Strieter, "The bimodal expression of tumor necrosis factor-α in association with rat lung reimplantation and allograft rejection," J. Immunol., 150(6):2494-2505, 1993. Faria and Weiner, "Oral tolerance: mechanisms and therapeutic applications," Adv. Immunol., 73:153-264, 1999. Fedoseyeva, Zhang, Orr, Levin, Buncke, Benichou, "De novo autoimmunity to cardiac myosin after heart transplantation and its contribution to the rejection process," J. Immunol., 162:6836-42, 1999. Garrovillo, Ali, Oluwole, "Indirect allorecognition in acquired thymic tolerance: induction of donor-specific tolerance to rat cardiac allografts by allopeptide-pulsed host dendritic cells," Transplantation, 68:1827-1834, 1999. Hancock, Sayegh, Kwok, Weiner, Carpenter, "Oral, but not intravenous, alloantigen prevents accelerated allograft rejection by selective intragraft Th2 cell activation," Transplantation, 55:1112-1118, 1993. Hanson, Gorman, Oui, Cheah, Solomon, Trowsdale, "The human α2(XI) collagen gene (COL11A2) maps to the centromeric of the major histocompatibility complex on chromosome 6," Genomics, 5:925-931, 1989. Hirt, You, Moller, Boeke, Starke, Spranger, Wottge, "Development of obliterative bronchiolitis after allogeneic rat lung transplantation: Implication of acute rejection and the time point of treatment," J. Heart Lung Transplant., 18:542-548, 1999. Huang, Fuchimoto, Scheier-Dolberg, Murphy, Neville, Sachs, J. Clin. Invest., 105:173-181, 2000. Ishido, Matsuoka, Matsuno, Nakagawa, Tanaka, "Induction of donor-specific hyporesponsiveness and prolongation of cardiac allograft survival by jejunal administration of donor splenocytes," Transplantation, 68:1377-1382, 1999. Iyer, Woo, Cornejo, Gao, McCoubrey, Maines, Buelow, "Characterization and biologic significance of immunosuppressive peptide D2702.75-84 (EαV) binding protein," J. Bio. Chem., 273(5):2692-2697, 1998. Joo, Pepose, Stuart, "T-cell mediated responses in a murine model of orthotopic corneal transplantation," Invest. Ophthalmol. Vis. Sci., 36:1530-1540, 1995. Konomi, Hayashi, Nakayasu, Arima, "Localization of type V collagen and type IV collagen in human cornea, lung, and skin," Am. J. Pathol., 116:417-426, 1984. Krensky and Clayberger, "HLA-derived peptides as novel immunosuppressives," Nephrol. Dial. Transplant., 12:865-878, 1997. Lowry, Marghesco, Blackburn, "Immune mechanisms in organ allograft rejection. VI. Delayed-type hypersensitivity and lymphotoxin in experimental renal allograft rejection," Transplantation., 40:183-188, 1985. Madri and Furthmayr, "Collagen polymorphism in the lung," Human Pathology, 11:353-366, 1980. Madri and Furthmayr, "Isolation and tissue localization of type AB2 collagen from normal lung parenchyma," Am. J. Pathol., 94:323-332, 1979. Marck, Prop, Widevuur, "Lung transplantation in the rat. III. Functional studies in iso- and allografts," J. Surgical Res., 35:149-158, 1983. Matsumura, Marchevsky, Zuo, Kass, Matloff, Jordan, "Assessment of pathological changes associated with chronic allograft rejection and tolerance in two experimental models of rat lung transplantation," Transplantation., 59:1509-1517, 1995. Morris and Bachinger, "Type XI collagen is a heterotrimer with the composition (1α,2α,3α) retaining non-triple helical domains. J. Biological Chem., 262:11345-11350, 1987. Murphy, Magee, Alexander, Waaga, Snoeck, Vella, Carpenter, Sayagh, "Inhibition of allorecognition by a human class II MHC-derived peptide through the induction of apoptosis," J. Clin. Invest., 103:859-867, 1999. Nosner, Goldberg, Naftzger, Lyu, Clayberger, Krensky, "HLA-derived peptides which inhibit T cell function bind to members of the heat-shock protein 70 family," J. Exp. Med., 183:339-348, 1996. Oluwole, Chowdhury, Jin, Hardy, "Induction of transplantation intolerance to rat cardiac allografts by intrathymic inoculation of allogeneic soluble peptides," Transplantation, 56(6): 1523-1527, 1993. Prop, Nieuwenhuis, Wildevuur, "Lung allograft rejection in the rat. I. Accelerated rejection caused by graft lymphocytes," Transplantation, 40:25-30, 1985. Prop, Wildevuur, Nieuwenhuis, "Lung allograft rejection in the rat. II. Specific immunological properties of lung grafts," Transplantation, 40:126-131, 1985. Sayagh, Watschinger, Carpenter, "Mechanisms of T cell recognition of alloantigen," Transplantation, 57:(9)1295-1302, 1994. Sayegh and Krensky, "Novel immunotherapeutic strategies using MHC derived peptides," Kidney Int. Suppl. 53:S13-20, 1996. Sayegh, Khoury, Hancock, Weiner, Carpenter, "Induction of immunity and oral tolerance with polymorphic class II major histocompatibility complex allopeptides in the rat," Proc. Natl. Acad. Sci., 89: 7762-7766, 1992. Sayegh, Zhang, Hancock, Kwok, Carpenter, Weiner, "Down-regulation of the immune response to histocompatibility antigens and prevention of sensitization by skin allografts by orally administered alloantigen," Transplantation, 53:163-166, 1992. Sekine, Nowen, Heidler, Van Rooijen, Brown, Cummings, Wilkes, "Role of passenger leukocytes in allograft rejection—Effect of depletion donor alveolar Macrophages on the local production of TNF-alpha, T helper 1/Thelper 2 cytokines, IgG subclasses, and pathology in a rat model of lung transplantation," J. Immunol, 159:4084-4093, 1997. Seyer and Kang, "Covalent structure of collagen: amino acid sequence of three cyanogen bromide-derived peptides from human alpha 1(V) collagen chain. Arch. Biochem. Biophys. 271(1): 120-129, 1989. SivaSai, Smith, Poindexter, Sundaresan, Trulock, Lynch, Cooper, Patterson, Mohanakumar, "Indirect recognition of donor HLA class I peptides in lung transplant recipients with bronchiolitis obliterans syndrome," Transplantation. 67(8):1094-1098, 1999. Smith Jr, Williams, Brandt, "Interaction of proteoglycans with pericellular (1 alpha, 2 alpha, 3 alpha) collagens of cartilage," J. Biol. Chem., 260: 10761-10767, 1985. Stark and Ostrow, Training Manual Series, Laboratory Animal Technician, American Association for Laboratory Animal Science, 181-182, 1990. Strober and Coffman, "Tolerance and immunity in the mucosal immune system," Res. Immunol., 148:489-599, 1997. Trulock, "Lung transplantation," Am. J. Respir. Crit. Care Med., 155:789-818, 1997. VanBuskirk, Wakely, Sirak, Orosz, "Patterns of allosensitization in allograft recipients: long-term allograft acceptance is associated with active alloantibody production in conjunction with active inhibition of alloreactive delayed-type hypersensitivity," Transplantation., 65:1115-1123, 1998. Westra, Prop, Kuijpers, "A paradox in heart and lung rejection," Transplantation, 49:826-828, 1990. Whitacre, Gienapp, Orosz, Bitar, "Oral tolerance in experimental autoimmune encephalomyelitis. III. Evidence for clonal anergy," J. Immunol., 147:2155-2163, 1991. Wilkes, Bowman, Cummings, Heidler, "Allogeneic bronchoalveolar lavage cells induce the histology and immunology of lung allograft rejection in recipient murine lungs. Role of ICAM-1 on donor cells," Transplantation, 67(6):890-896, 1999. Wilkes, Heidler, Bowen, Quinlan, Doyle, Cummings, Doerschuk, "Allogeneic bronchoalveolar lavage cells induce the histology of acute lung allograft rejection, and deposition of IGg2a in recipient murine lungs," J. Immunol., 155:2775-2783, 1995. Wilkes, Thompson, Cummings, Bragg, Heidler, "Instillation of allogeneic lung macrophages and dendritic cells cause differential effects on local IFY-γ production, lymphocytic bronchitis, and vasculitis in recipient murine lungs," J. Leukoc. Biol. 64:578-586, 1998. Wilson, Ebringer, Ahmadi, Wrigglesworth, Tiwana, Fielder, Binder, Ettelaie, Cunningham, Joannou, Bansal," "Shared amino acid sequences between major histocompatibility complex class II glycoproteins, type XI collagen and *Proteus mirabilis* in rheumatoid arthritis," Ann. Rheum. Dis.," 54:216-220, 1995. Woessner Jr., "The determination of hydroxyproline in tissue and protein samples containing small proportions of this immino acid," Arch. Biochem. Biophys. 93:440-447, 1961. Yagyu, Steinhoff, Schafers, Dammenhayn, Haverich, Borst, "Comparison of mononuclear cell populations in brochoalveolar lavage fluid in acute rejection after lung transplantation and *Mycoplasma* infection in rats," J. Heart Transplant., 9:516-525, 1990. Yamagami, Tsuru, Ohkawa, Endo, Isobe, "Suppression of allograft rejection with anti-alpha beta T cell receptor antibody in rat corneal transplantation," Transplantation, 67:600-604, 1999. Yoshino, Quattrocchi, Weiner, "Suppression of antigen-induced arthritis in Lewis rats by oral administration of type II collagen," Arthritis Rheum. 38: 1092-1096, 1995. Yousem, Berry, Cagle, Chamberlain, Husain, Hruban, Marchevsky, Ohori, Ritter, Stewart, Tazelaar," "Revision of the 1990 working formulation for the classification of pulmonary allograft rejection: Lung rejection study group," J. Heart Lung Transplant, 15:1-15, 1996. Zheng, Markees, Hancock, Li, Greine, Li, Mordes, Sayegh, Rossini, Strom, "CTLA4 signals are required to optimally induce allograft tolerance with combined donor-specific transfusion and anti-CD154 monoclonal antibody treatment," J. Immunol., 162:4983-4990, 1999.

EXAMPLES

Example 1

Anti-Collagen V Antibodies are Increased in COPD Patients

Plasma was obtained from normal volunteers (non smoking adults, age 18-55), and volunteers with documented emphysema. Levels of anti-colV antibodies in COPD patients and control healthy subjects were detected by the flow cytometry bead assay as described in WO 2007/120947.

Briefly, 1) Streptavidin-coated beads (5 µm, binding capacity 10-20 µg/1×10$^7$ beads (Polyscience, Warrington, Pa.)) were washed two times with sterile PBS. Beads (1×10$^7$) were suspended in 100 µl of PBS with 40 µg of human Type V collagen and incubated for 60 minutes at 4° C. 2) A positive control was generated by following the same procedures in 1 above, using 20 µm of rabbit antibody to human collagen V antibody (bioten) (Abeam, Cambridge, Mass.). 3) For each assay, 1×10$^6$ conjugated beads were washed two times in PBS, and incubated in 100 µl PBS plus 50 µl serum. After incubating for 30-minutes at room temperature, the beads were washed three times with PBS containing 10% FCS. 4) The beads were suspended in 100 µl of sterile PBS+10% FBS and incubated for about 30 minutes at room temperature with secondary antibody. Typically, 5 µl of anti-human IgG antibody conjugated with R-PE was used (Sigma, Saint Louis). The beads were washed three times in PBS containing 10% FCS, suspended in 300 µl of PBS/FCS solution and analyzed using a flow cytometer.

Figure 1:
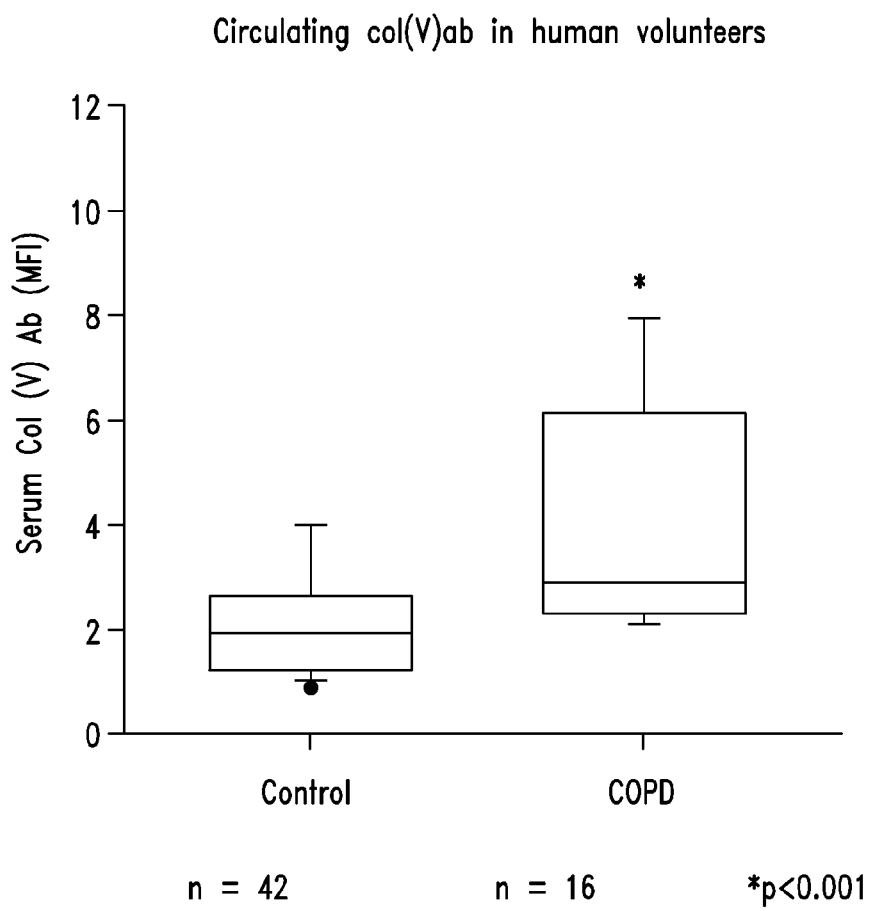
FIG. 1 is a bar graph showing elevated anti-type V collagen antibodies in COPD patients.

As shown in FIG. 1, anti-type V collagen antibodies are significantly elevated in COPD patients (N=16) as compared to controls (N=42).

Example 2

Anti-Collagen V Antibodies are Increased in Asthma Patients

Plasma was obtained from normal volunteers (non smoking adults, age 18-55), and volunteers with documented chronic asthma. Levels of anti-colV antibodies in the asthma patients and control volunteer subjects were measured using the bead assay as outlined in Example 1.

Figure 2:
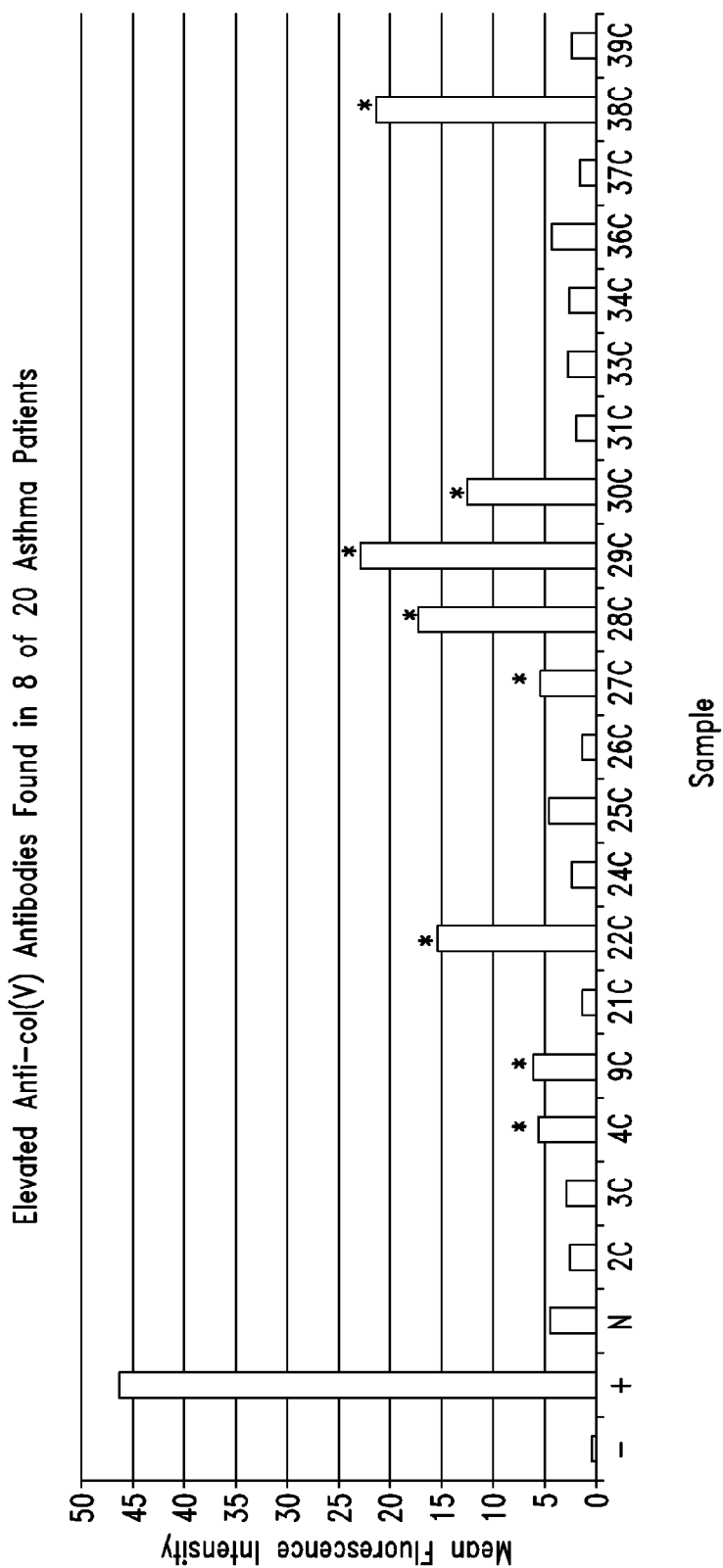
FIG. 2 is a bar graph showing elevated anti-type V collagen antibodies in asthma patients.

As shown in FIG. 2, elevated levels of anti-type V collagen antibodies were found in 8 of 20 asthmatics.

Example 3

Intravenous Collagen V Prevents Ovalbumin-Induced Airway Hyper-Responsiveness in Mice This Example demonstrates that intravenous administration of collagen V prevents ovalbumin-induced airway hyper-responsiveness in this well-established murine asthma model.

Balb/c mice were injected via tail vein with 100 µg col (V), alone, or col(V) mixed in complete Freund's adjuvant, (CFA), or PBS, or CFA, alone. Seven days later mice received an IP injection of ovalbumin in alum and this was repeated seven days later. Seven days after the last ova/alum injection, mice in each group were challenged with increasing doses of aerosolized ova followed by measurements of airways resistance (PenH).

The results showed that col(V), alone, abrogated ova-induced airway hyperresponsiveness (see FIG. 3). Further experiments were conducted which confirm these results. These results are summarized below in Table 2.

TABLE 2

Col(V) alone abrogates ova-induced airway hyperresponsiveness

| Mg/ml methacholine | PBS PenH Units | | | Col(V) PenH Units | | | 2-WAY ANOVA |
| --- | --- | --- | --- | --- | --- | --- | --- |
| | Mean | SEM | N | Mean | SEM | N | P value |
| Baseline | 0.419913 | 0.021817 | 6 | 0.564856 | 0.092752 | 6 | >0.05 |
| Saline | 0.466943 | 0.034769 | 6 | 0.519667 | 0.073273 | 6 | >0.05 |
| 10 | 1.413495 | 0.189206 | 6 | 1.615039 | 0.172871 | 6 | >0.05 |
| 25 | 2.448044 | 0.438264 | 6 | 2.914945 | 0.510278 | 6 | >0.05 |
| 50 | 4.463914 | 0.319439 | 6 | 3.147791 | 0.531683 | 6 | >0.05 |
| 100 | 5.121152 | 0.327822 | 6 | 3.661426 | 0.544324 | 6 | >0.05 |
| 200 | 6.064105 | 0.368829 | 6 | 3.387585 | 0.46153 | 6 | <0.001 |
| 300 | 6.825607 | 0.499452 | 6 | 3.700204 | 0.657257 | 6 | <0.001 |

Example 4

Intravenous Col(V) Induces IFN-γ Transcripts in Lung Mononuclear Cells

This example shows intravenous injection of col(V) alone induced a TH1 response in lung mononuclear cells, characterized by induction of IFN-γ transcripts. Balb/c mice were injected via tail vein with 100 ug col(V) alone, CFA alone at the base of the tail, colV plus CFA the base of the tale or PBS i.v. alone. Seven days later mice received an IP injection of ovalbumin in alum and this was repeated seven days later. Seven days after the last ova/alum injection, mice in each group were challenged with increasing doses of aerosolized methacholine followed by measurements of airways resistance in response to methacholine challenge (PenH). RNA was extracted from mononuclear cells isolated from the lung parenchyma of mice in each treatment group and quantitative PCR performed for determining expression levels of IL-4, IL-5, IL-13, IFN-γ and IL-10 (see FIG. 4; data represent lung mononuclear cells of RNA pooled from 5 mice in each group).

The results of the experiment show that Col(V) alone administered intravenously induced IFN-γ transcripts in lung mononuclear cells. IFN-γ is antagonistic to IL-13 and IL4, two cytokines thought to play a key role in asthma pathogenesis. Therefore, without being bound by theory, induction of this TH1 response which counteracts the effects of IL4/IL13 may play a part in the colV-mediated protective effect in ova-induced asthma.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. A method of treating an individual having or suspected of having asthma, comprising administering to the individual a therapeutically effective amount of type V collagen.

2. The method of claim 1, wherein the type V collagen is administered by a route selected from the group consisting of oral administration, intravenous administration, intrapulmonary instillation, administration by inhalation, and intramuscular administration.

3. The method of claim 2, wherein the therapeutically effective amount of type V collagen is between 0.1 mg and 0.5 mg of type V collagen.

4. The method of claim 1, further comprising co-administering a bronchodilator.

5. The method of claim 1, wherein the therapeutically effective amount of type V collagen is between 0.001 mg and 1.0 mg.

6. The method of claim 1, wherein the therapeutically effective amount of type V collagen is between 0.01 mg and 0.8 mg.

7. The method of claim 1, wherein the therapeutically effective amount of type V collagen is administered daily as a single dose.

* * * * *